United States Patent
Ku et al.

(10) Patent No.: US 12,092,575 B2
(45) Date of Patent: Sep. 17, 2024

(54) MEASURING METHOD OF CELL MIGRATION USING THE RATE OF CELL INVASION

(71) Applicants: MBD Co., Ltd., Suwon-si (KR); SAMSUNG LIFE PUBLIC WELFARE FOUNDATION, Seoul (KR); Research & Business Foundation SUNGKYUNKWAN UNIVERSITY, Suwon-si (KR)

(72) Inventors: Bo Sung Ku, Yongin-si (KR); Jung Eun Kim, Yongin-si (KR); Man Ki Chung, Seoul (KR); Dong Woo Lee, Daejeon (KR)

(73) Assignees: MBD Co., Ltd., Suwon-si (KR); SAMSUNG LIFE PUBLIC WELFARE FOUNDATION, Seoul (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 261 days.

(21) Appl. No.: 17/739,403

(22) Filed: May 9, 2022

(65) Prior Publication Data
US 2022/0373462 A1    Nov. 24, 2022

(30) Foreign Application Priority Data

May 14, 2021    (KR) .................. 10-2021-0062382
Aug. 12, 2021   (KR) .................. 10-2021-0106494

(51) Int. Cl.
G01N 21/64    (2006.01)
C12M 1/32     (2006.01)
G01N 33/50    (2006.01)

(52) U.S. Cl.
CPC ............ G01N 21/64 (2013.01); C12M 23/12 (2013.01); G01N 33/5005 (2013.01); G01N 2021/6439 (2013.01)

(58) Field of Classification Search
None
See application file for complete search history.

(56) References Cited

U.S. PATENT DOCUMENTS 9,121,847 B2 *  9/2015  Kamm ................... C12M 41/46
9,267,103 B2 *  2/2016  Lichtenberg ......... B01L 3/50855
(Continued)

FOREIGN PATENT DOCUMENTS

KR    10-2069726    1/2020

OTHER PUBLICATIONS

Lim, Gippeum J., et al. "Novel invasion indices quantify the feed-forward facilitation of tumor invasion by macrophages." Scientific reports 10.1 (Jan. 20, 2020): 718. pp. 1-10.
(Continued)

*Primary Examiner* — David P Porta
*Assistant Examiner* — Djura Malevic
(74) *Attorney, Agent, or Firm* — LEX IP MEISTER, PLLC

(57) ABSTRACT

The present invention is directed to a method of measuring cell migration by measuring the invasion ratio of cells incubated on a pillar array inserted into a well structure, the method including steps of: preparing a pillar array having a plurality of micropillars and a well structure having a plurality of microwells into which the plurality of micropillars is insertable, respectively; forming cell spheroids by incubating cells in an extracellular matrix attached to the end contact surfaces of the micropillars; allowing the cells contained in the cell spheroids to invade the end contact
(Continued)

surfaces; staining and scanning the cell spheroids, the cells contained in the cell spheroids, and the cells that invaded the end contact surfaces; and calculating the invasion ratio of cells by the following equation through a fluorescence image of the scanned cells:

$$\text{Invasion Ratio} = \frac{\text{Invasion cell area}}{\text{Total cell area}} = \frac{A_{Total} - A_{spheroid}}{A_{Total}} \quad \text{[Equation]}$$

wherein $A_{total}$ represents the total cell area, and $A_{spheroid}$ represents the spheroid area.

8 Claims, 22 Drawing Sheets

(56) References Cited

U.S. PATENT DOCUMENTS

| | | | |
|---|---|---|---|
| 9,488,641 B2* | 11/2016 | Gratzl | G01N 27/3277 |
| 9,506,907 B2* | 11/2016 | Bergkvist | C12N 5/0621 |
| 9,750,826 B2* | 9/2017 | Nam | A61K 49/0008 |
| 10,073,346 B2* | 9/2018 | Hribar | G01N 33/5008 |
| 10,423,071 B2* | 9/2019 | Hribar | G03F 7/7015 |
| 10,605,708 B2* | 3/2020 | Shao | B01D 63/081 |
| 10,648,975 B2* | 5/2020 | Xu | G01N 33/54388 |
| 11,390,836 B2* | 7/2022 | Lee | C12M 23/12 |
| 11,554,370 B2* | 1/2023 | Khurana | B01L 3/502715 |
| 11,773,357 B2* | 10/2023 | Lee | C12M 21/08 435/370 |
| 11,918,605 B1* | 3/2024 | Wagner | C12N 5/0645 |
| 2004/0142411 A1* | 7/2004 | Kirk | B82Y 30/00 435/288.5 |
| 2004/0259177 A1* | 12/2004 | Lowery | C12M 23/16 435/7.23 |
| 2005/0169962 A1* | 8/2005 | Bhatia | G01N 33/5067 435/366 |
| 2005/0260745 A1* | 11/2005 | Domansky | B01L 3/50255 435/294.1 |
| 2006/0136182 A1* | 6/2006 | Vacanti | C12M 25/14 703/11 |
| 2007/0015274 A1* | 1/2007 | Shuler | C12M 41/46 435/293.1 |
| 2007/0099294 A1* | 5/2007 | Yang | C12M 23/12 435/288.5 |
| 2007/0128715 A1* | 6/2007 | Vukasinovic | C12M 23/22 435/303.1 |
| 2008/0063851 A1* | 3/2008 | Jackman | B82Y 30/00 428/220 |
| 2011/0159522 A1* | 6/2011 | Kamm | G01N 33/5029 435/287.1 |
| 2011/0186165 A1* | 8/2011 | Borenstein | C12M 23/16 156/196 |
| 2012/0135890 A1* | 5/2012 | Shin | B01L 3/5088 506/18 |
| 2012/0165224 A1* | 6/2012 | Song | C40B 60/12 506/13 |
| 2013/0203146 A1* | 8/2013 | Ying | C12N 5/0062 435/177 |
| 2014/0141503 A1* | 5/2014 | Hong | C12M 23/10 427/256 |
| 2014/0154722 A1* | 6/2014 | Yeal | C12M 23/12 435/174 |
| 2014/0322806 A1* | 10/2014 | Bennett | C12M 29/04 435/325 |
| 2015/0057184 A1* | 2/2015 | Bhatia | C12M 25/14 506/40 |
| 2015/0086445 A1* | 3/2015 | Lee | C12M 33/02 422/503 |
| 2015/0101070 A1* | 4/2015 | Nam | G01N 33/5011 800/3 |
| 2015/0104391 A1* | 4/2015 | Nam | A61K 49/0008 424/9.2 |
| 2015/0175972 A1* | 6/2015 | Jabbari | C12N 5/0695 435/382 |
| 2015/0268223 A1* | 9/2015 | Bhatia | G01N 33/5014 435/7.1 |
| 2015/0314613 A1* | 11/2015 | Murphy | C12M 33/12 435/283.1 |
| 2016/0010054 A1* | 1/2016 | Gartner | C12N 11/00 435/174 |
| 2016/0115457 A1* | 4/2016 | Kim | C12N 5/0062 435/373 |
| 2016/0175800 A1* | 6/2016 | Murphy | G01N 33/5026 506/18 |
| 2016/0178611 A1* | 6/2016 | Han | G01N 33/5011 435/32 |
| 2016/0289851 A1* | 10/2016 | Majdzarringhalamaraghy | C25D 5/02 |
| 2016/0298087 A1* | 10/2016 | Qu | C12N 5/0671 |
| 2017/0067025 A1* | 3/2017 | Nikkhah | C12N 5/0012 |
| 2017/0198275 A1* | 7/2017 | Lee | C12Q 1/02 |
| 2017/0252486 A1* | 9/2017 | Shastri | A61L 27/50 |
| 2017/0267960 A1* | 9/2017 | Tsukada | B01L 3/5085 |
| 2018/0348637 A1* | 12/2018 | Hribar | G03F 7/20 |
| 2019/0155146 A1* | 5/2019 | Hribar | G03F 7/16 |
| 2022/0373462 A1* | 11/2022 | Ku | G01N 33/5005 |

OTHER PUBLICATIONS

Lee, Sangyun, et al. "3D-Hepatocellular Carcinoma (3D-HCC) Models of Diffused and Aggregated Spheroids using a 96-Pillar/Well Plate." Research Square (posted on Feb. 19, 2021). pp. 1-24.

* cited by examiner

Incubating Cells for 4 days
to form single spheroid

Treating drugs for 3 days

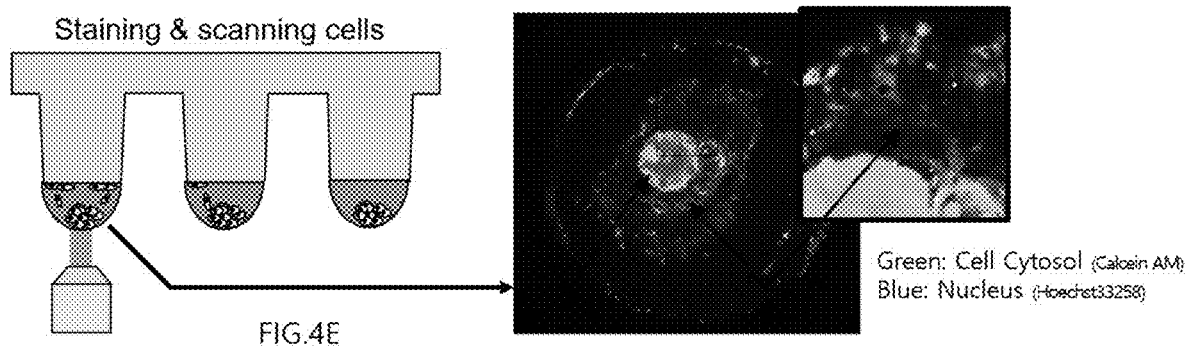
FIG. 4E
FIG. 5
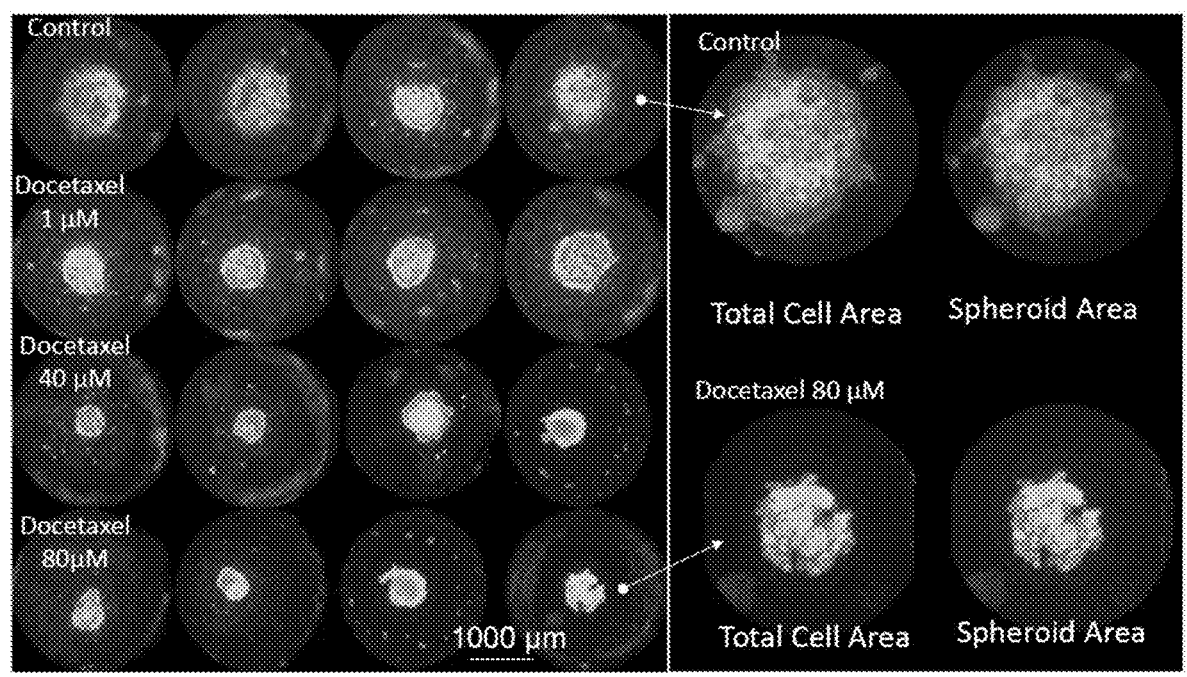

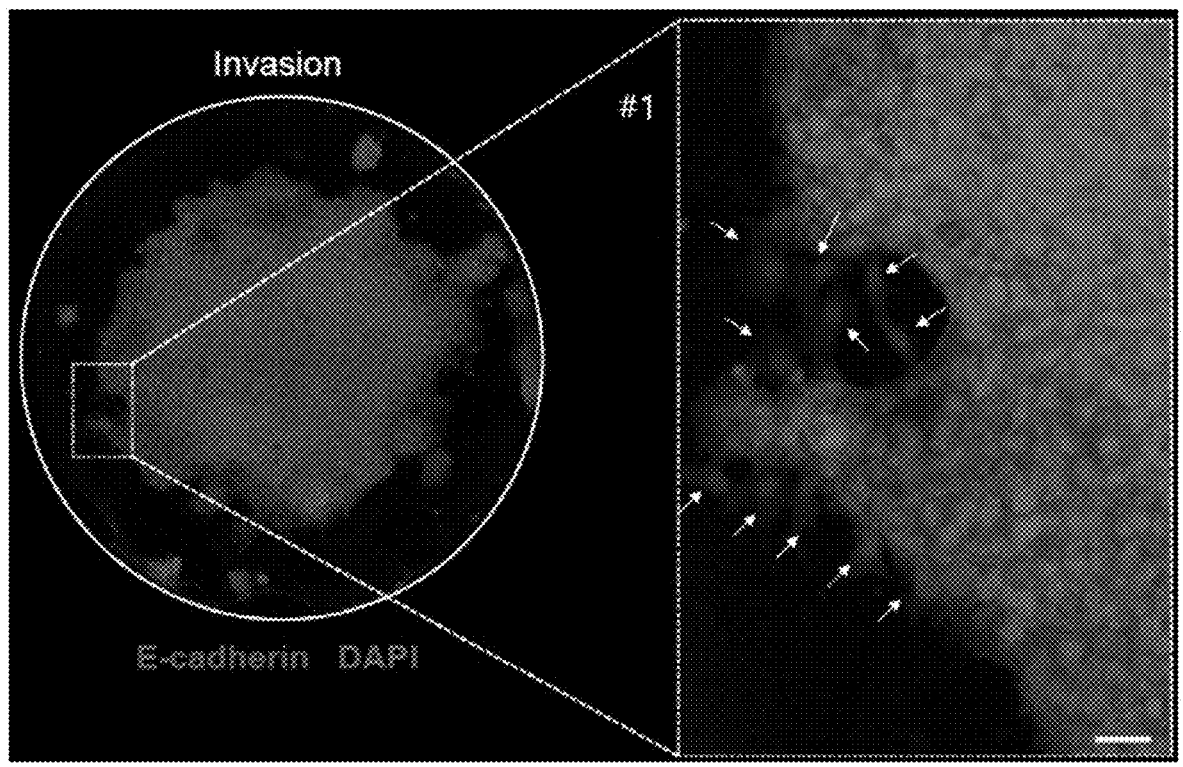
FIG.10B
FIG. 11
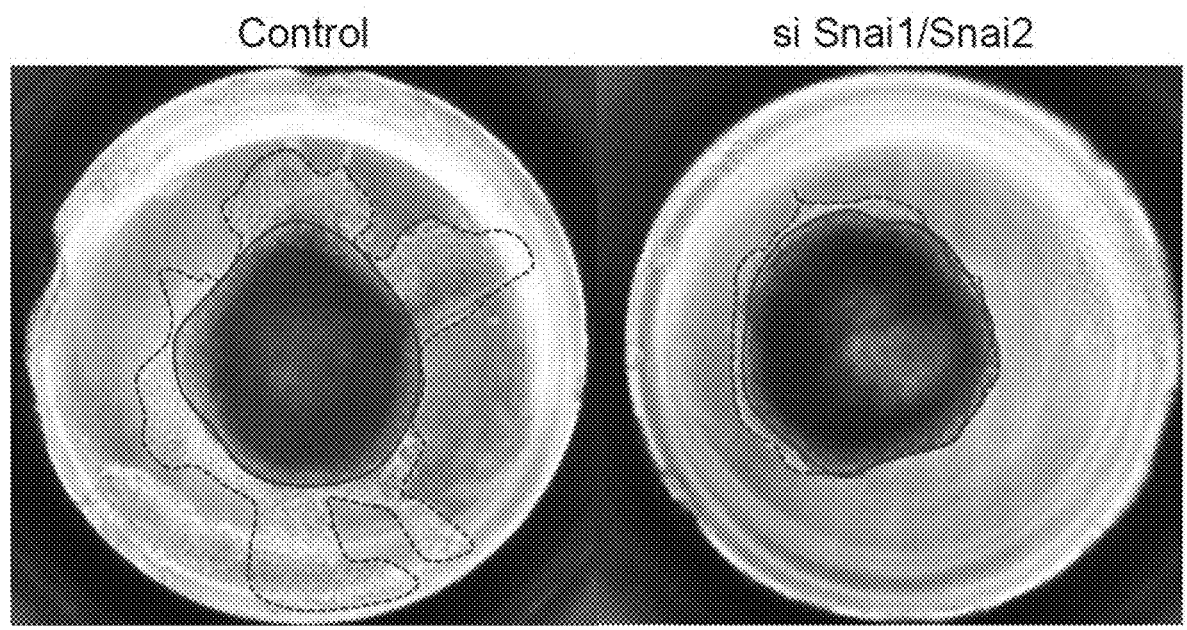

FIG. 22

| Step of preparing a pillar array having a plurality of micropillars and a well structure having a plurality of microwells into which the plurality of micropillars is insertable, respectively | ~S1 |

↓

| Step of forming cell spheroids by incubating cells in an extracellular matrix attached to the end contact surfaces of the micropillars | ~S2 |

↓

| Step of allowing the cells contained in the cell spheroids to invade the end contact surfaces | ~S3 |

↓

| Step of staining and scanning the cell spheroids and the cells that invaded the end contact surfaces of the micropillars | ~S4 |

↓

| Step of calculating the invasion ratio of cells through a fluorescence image of the scanned cells | ~S5 |

MEASURING METHOD OF CELL MIGRATION USING THE RATE OF CELL INVASION

CROSS-REFERENCE TO RELATED APPLICATION

This application claims the benefit of Korean Patent Application No. 10-2021-0106494 filed on Aug. 12, 2021, which is hereby incorporated by reference herein in its entirety.

BACKGROUND

1. Technical Field

The present invention relates to a method for measuring cell migration. More specifically, the present invention relates to a method of measuring cell migration using the invasion ratio of cells.

2. Description of the Related Art

Cell migration is a process in which cells move from one place to another, and refers to the movement of a series of cells or individual cells due to various physical, chemical, and biological stimuli. Such cell migration is deeply associated with various biological phenomena such as angiogenesis, cancer metastasis, tissue development and differentiation, damaged tissue regeneration, and immune responses, as well as the treatment of various diseases.

Korean Patent No. 10-2069726 discloses a technology of measuring cell migration by measuring the frequency at which cells move and adhere to the contact surface of a micropillar chip, which is a specific location.

However, this conventional art relies upon whether or not cells adhere, and when the extent of the actual area to which cells adhere is different, a problem arises in that it is not possible to distinguish the difference in the degree of cell migration and invasion.

In addition, in the case of cells that adhered to the contact surface of the pillar chip, there is a problem in that the initial position of the cells in the initial extracellular matrix (Matrigel, etc.) is different, and thus the actual cell migration distance differs depending on the initial position of the cells, making it difficult to accurately measure the extent of cell migration.

RELATED ART DOCUMENT

Patent Document (Patent Document 1) Korean Patent No. 10-2069726 (published on Jan. 17, 2020)

SUMMARY

A method of measuring cell migration using the invasion ratio of cells according to the present invention achieves the following objects:

A first object of the present invention is to measure the invasion ratio, which is the degree of cell migration and invasion.

A second object of the present invention is to form spheroids by gathering cells to be incubated in a certain portion of an extracellular matrix, in order to uniformize the actual migration distance of cells attached to the end contact surfaces of micropillars.

Objects of the present invention are not limited to the above-mentioned objects, and other objects not described herein will be clearly understood by those skilled in the art from the following description.

The present invention provides a method of measuring cell migration by measuring the invasion ratio of cells incubated on a pillar array inserted into a well structure, the method including steps of: (S1) preparing a pillar array having a plurality of micropillars and a well structure having a plurality of microwells into which the plurality of micropillars are insertable, respectively; (S2) forming cell spheroids by incubating cells in an extracellular matrix attached to the end contact surfaces of the micropillars of the pillar array; (S3) allowing cells contained in the cell spheroids to invade the end contact surfaces of the micropillars; (S4) staining and scanning the cell spheroids, the cells contained in the cell spheroids, and the cells that invaded the end contact surfaces of the micropillars; and (S5) calculating the invasion ratio of cells by the following Equation through a fluorescence image of the scanned cells:

$$\text{Invasion Ratio} = \frac{\text{Invasion cell area}}{\text{Total cell area}} = \frac{A_{Total} - A_{spheroid}}{A_{Total}} \quad \text{[Equation]}$$

wherein $A_{total}$ represents the total cell area, and $A_{spheroid}$ represents the spheroid area.

In the present invention, step (S2) may include steps of: (S2-1) placing the pillar array so that the end contact surfaces of the micropillars face upward, and dispensing and attaching the cell-containing extracellular matrix to the end surface surfaces; (S2-2) placing the pillar array upside down so that the end contact surfaces of the micropillars face downward, and gathering the cells by maintaining the end contact surfaces in the downward-facing state for a predetermined time in a state in which the micropillars are inserted or not inserted into the microwells; and (S2-3) inserting the micropillars into the microwells containing a culture medium in a state in which the end contact surfaces face downward, and forming cell spheroids by incubating the cells contained in the extracellular matrix.

In the present invention, the extracellular matrix may include Matrigel.

In the present invention, in step (S2-2), the state in which the end contact surfaces of the micropillars face downward may be maintained at 4° C. for 20 minutes.

In the present invention, in steps (S2-2) and (S2-3), the cells may be gathered at the lower end of the extracellular matrix.

In the present invention, in step (S2-3), the incubation may be performed at 37° C. under 5% $CO_2$.

In the present invention, in step (S3), $A_{total}$ represents the total cell area corresponding to a low-intensity area (higher than 20 code green intensity), and $A_{spheroid}$ represents the spheroid area corresponding to a high-intensity area (exceeding 60 code green intensity).

In the present invention, step (S3) may include steps of: (S3-1) withdrawing the micropillars, which have the formed cell spheroids thereon, from the microwells; (S3-2) inserting the micropillars again into the microwells 210 containing a predetermined drug in a state in which the end contact surfaces of the withdrawn micropillars face downward; and (S3-3) allowing the cells contained in the cell spheroids to migrate, invade and adhere to the end contact surfaces of the micropillars inserted again.

In the present invention, the drug in step (S3-2) may be a cancer therapeutic agent.

The method of measuring cell migration using the invasion ratio of cells according to the present invention has the following effects:

First, the invasion ratio of cells is accurately calculated by staining and scanning the cell spheroids, the cells contained in the cell spheroids, and the cells that invaded the end contact surfaces of the micropillars.

Second, cell spheroids are easily formed by placing the end contact surfaces of the micropillars to face downward.

Third, by gathering the cells to be incubated at the lower end of the extracellular matrix, the actual migration distance of the cells is precisely measured.

Effects of the present invention are not limited to the above-mentioned effects, and other effects not described herein will be clearly understood by those skilled in the art from the following description.

BRIEF DESCRIPTION OF THE DRAWINGS

FIG. 4E shows an example of step S4 regarding cell staining and scanning;

FIG. 5 shows images of viable spheroids on pillars with three different concentrations of docetaxel;

FIG. 10A shows representative images of E-cadherin expressions (red) in FaDu spheroid using pillar assay and FIG. 10B depicts image showing invaded FaDu cells from spheroid, wherein the arrows thereof indicate invaded FaDu cells with decreased E-cadherin expression;

FIG. 11 shows invasion assays performed on FaDu cells transfected with Snai1 and Snai2 siRNAs;

FIG. 22 is a flow chart showing a method of measuring cell migration using the invasion ratio of cells according to the present invention.

DETAILED DESCRIPTION

Figure 1:
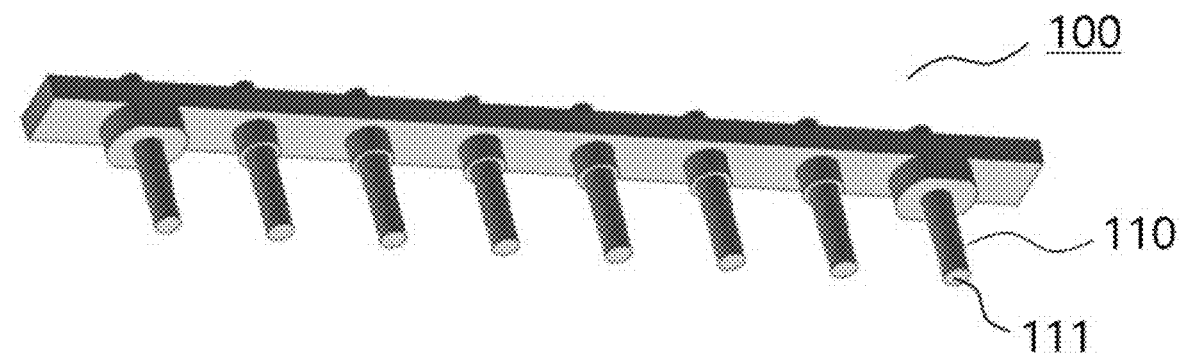
FIG. 1 illustrates an example of a pillar array according to the present invention.

Embodiments of the present invention will be described below with reference to the accompanying drawings so that the present invention can be easily carried out by those of ordinary skill in the art to which the present invention pertains. As can be easily understood by those of ordinary skill in the art to which the present invention pertains, the embodiments described below may be modified in various forms without departing from the concept and scope of the present invention. Throughout the drawings, the same or similar parts are denoted by the same reference numerals whenever possible.

The terminology used herein is intended to describe particular embodiments only, but is not intended to limit the scope of the present invention. Singular forms used herein are intended to include plural forms as well, unless the context clearly indicates otherwise.

The terms "include" and/or "including" used herein specify the presence of stated features, regions, integers, steps, operations, elements, components, and/or groups thereof, but do not preclude the presence or addition of one or more other features, regions, integers, steps, operations, elements, components and/or groups thereof.

The directional terms, such as up, down, left and right, used herein may be interpreted based on the drawings.

All terms used herein, including technical and scientific terms, have the same meaning as commonly understood by those of ordinary skill in the art to which the present invention pertains. The terms used in general and defined in dictionaries should be interpreted as having meanings identical to those specified in the context of related technology and in the present invention. Unless otherwise defined, the terms are not to be interpreted as having ideal or excessively formative meanings.

The present invention relates to a method for measuring cell migration. The term "cells" as used herein refers to animal cells capable of migration. For example, the cells may be cancer cells, including primary tumor cells, invasive cells and metastatic cells. The cancer includes metastatic cancer or metastasis inducible cancer.

Regarding cancer, the method of the present invention may be used for the measurement of migration of various cancer cells, including acute myeloid leukemia (AML), breast cancer (BRCA), cholangiocarcinoma (CCC), chronic lymphocytic leukemia (CLL), colorectal cancer (CRC), gallbladder cancer (GBC), glioblastoma. (GBM), gastric cancer (GC), gastroesophageal junction cancer (GEJC), hepatocellular carcinoma (HCC), head and neck squamous cell carcinoma (HNSCC), melanoma (MEL), non-Hodgkin's lymphoma (NHL), non-small cell lung cancer (NSCLC), ovarian cancer (OC), esophageal cancer (OSCAR), pancreatic cancer (PACA), prostate cancer (PRCA), renal cell carcinoma (RCC), small cell lung cancer (SCLC), bladder carcinoma (UBC) and endometrial cancer (UEC).

The present invention will be described below with reference to the drawings. For reference, the drawings may be partially exaggerated in size in order to explain the features of the present invention. In this case, it is preferable to perform interpretation in light of the entire purpose of the present specification.

FIG. 22 is a flow chart showing a method of measuring cell migration using the invasion ratio of cells according to the present invention.

As shown in FIG. 22, the method for measuring cell migration according to the present invention includes steps of: (S1) preparing a system; (S2) forming cell spheroids; (S3) allowing cells to invade; (S4) staining and scanning cells; and (S5) calculating the invasion ratio of cells.

The present invention provides a method for measuring the invasion ratio of cells incubated on a pillar array 100 inserted into a well structure 200, the method including steps of: (S1) preparing a pillar array 100 having a plurality of micropillars 110 and a well structure 200 having a plurality of microwells 210 into which the plurality of micropillars 110 are insertable, respectively; (S2) forming cell spheroids by incubating cells in an extracellular matrix attached to the end contact surfaces 111 of the pillar array 110; (S3) allowing cells contained in the cell spheroids to invade the end contact surfaces 111 of the micropillars 110; (S4) staining and scanning the cell spheroids and the cells that invaded the end contact surfaces 111 of the micropillars; and (S5) calculating the invasion ratio of cells by the Equation through a fluorescence image of the scanned cells.

Step (S1) according to the present invention is a step of preparing a pillar array 100 having a plurality of micropillars 110 and a well structure 200 having a plurality of microwells 210 into which the plurality of micropillars 110 are insertable, respectively.

Figure 2:
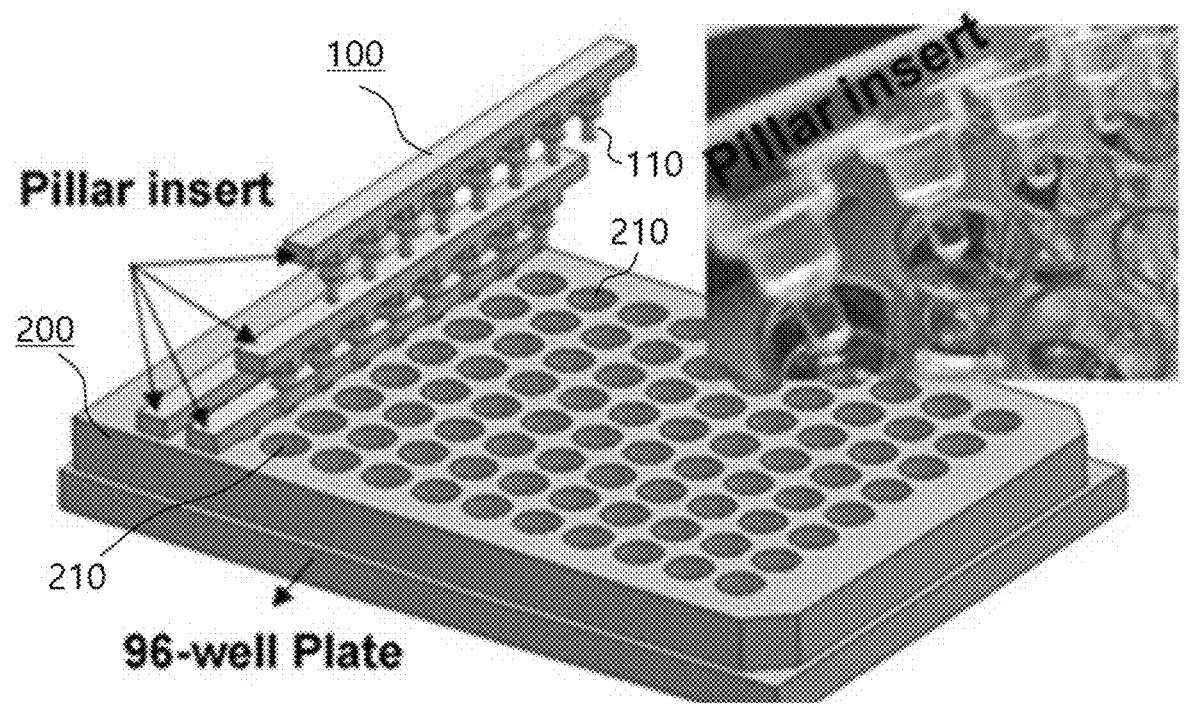
FIG. 2 is a schematic view showing a state in which the pillar array according to the present invention is coupled to a well structure.

In step (S1) according to the present invention, the pillar array illustrated in FIG. 1 is used. FIG. 2 is a schematic view showing that the pillar array according to the present invention is coupled to a well structure.

Step (S2) according to the present invention is a step of forming cell spheroids by incubating cells in an extracellular matrix attached to the end contact surfaces 111 of the micropillars 111 of the pillar array 110

As used herein, the term "cell spheroid" refers to a circular aggregate of a plurality of cells aggregated in a lump shape.

Figure 4A:
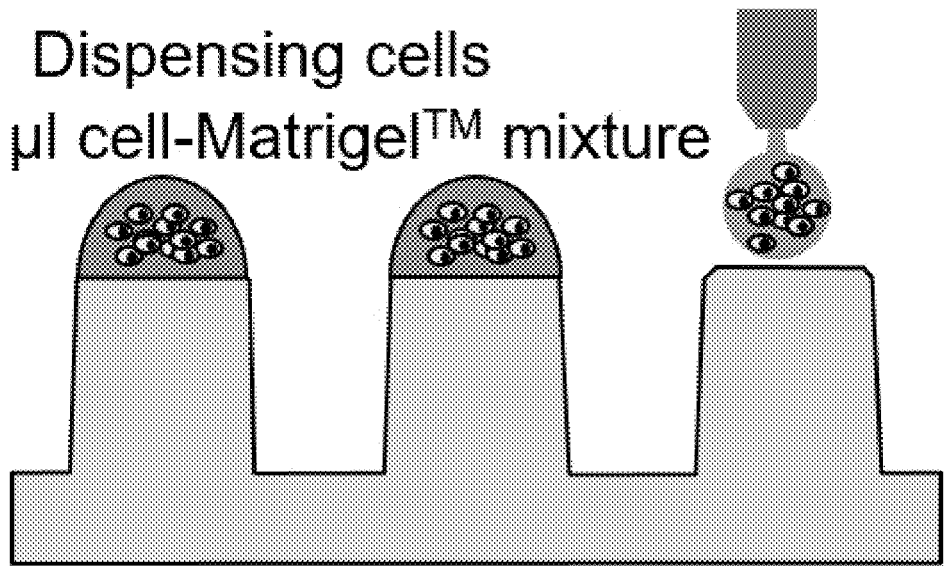
FIGS. 4A, 4B and 4C show an example of step S2 regarding cell spheroid formation.
Figure 4B:
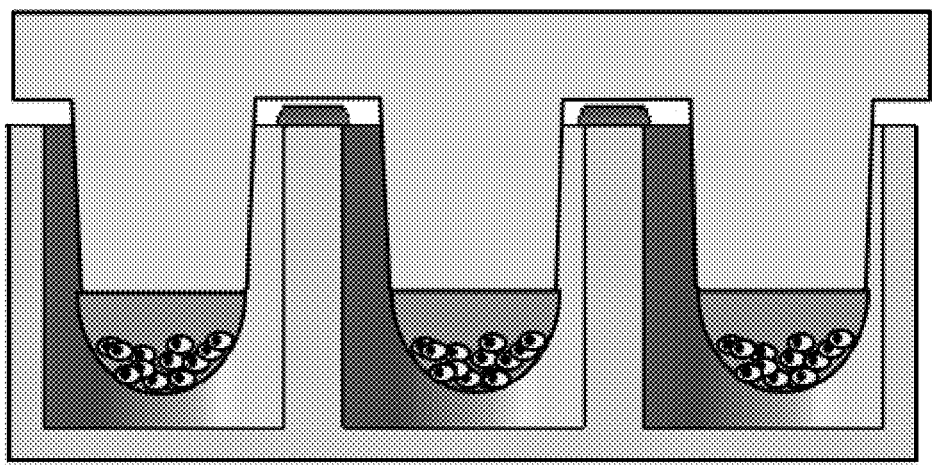
Figure 4C:
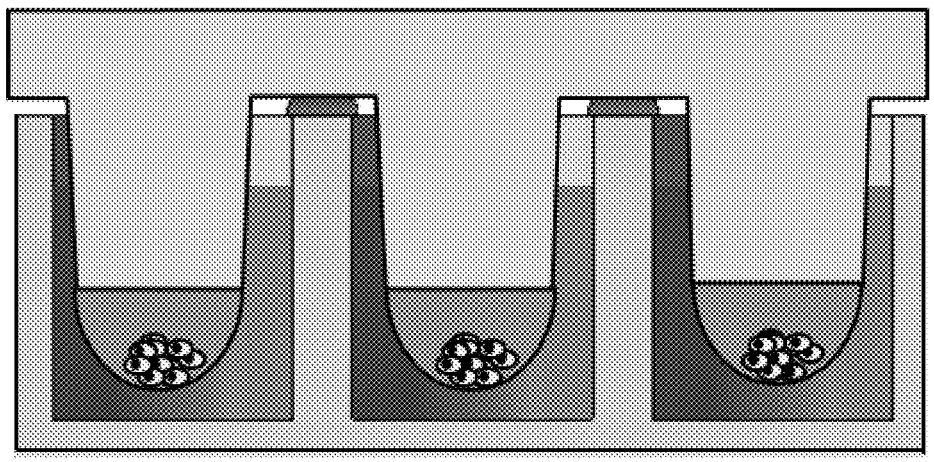

FIGS. 4A, 4B and 4C show an example of step S2 regarding cell spheroid formation.

Step (S2) according to the present invention includes steps of: (S2-1) placing the pillar array 100 so that the end contact surfaces 111 of the micropillars 110 face upward, and dispensing and attaching the cell-containing extracellular matrix to the end surface surfaces; (S2-2) placing the pillar array 100 upside down so that the end contact surfaces 111 of the micropillars 110 face downward, and gathering the cells by maintaining the end contact surfaces in the downward-facing state for a predetermined time in a state in which the micropillars 110 are inserted or not inserted into the microwells 210; and (S2-3) inserting the micropillars 110 into the microwells 210 containing a culture medium in a state in which the end contact surfaces 111 face downward, and forming cell spheroids by incubating the cells contained in the extracellular matrix.

The mixture dispensed in step (S2-1) according to the present invention is a mixture of extracellular matrix and cells. The extracellular matrix includes Matrigel.

Step (S2-2) according to the present invention may be performed in a state in which the micropillars 110 are inserted into the microwells 210. On the other hand, in a state in which the micropillars 110 are inserted into the microwells 210, concerns about contamination may arise. As long as contamination is prevented, step (S2-2) may be performed in a state in which the micropillars 110 are not inserted into the microwells 210.

In step (S2-2) according to the present invention, the state in which the end contact surfaces 111 of the micropillars 110 face downward may be maintained at 4° C. for 20 minutes.

In step (S2-3) according to the present invention, the incubation may be performed at 37° C. under 5% $CO_2$.

In steps (S2-2) and (S2-3), the cells may be gathered at the lower end of the extracellular matrix.

In step (S2-2), the cells may be gathered downward by gravity, and the cells gathered in step S2-3 may form cell spheroids.

Step (S3) according to the present invention is a step of allowing cells contained in the cell spheroids to invade the end contact surfaces 111 of the micropillars 110.

Figure 4D:
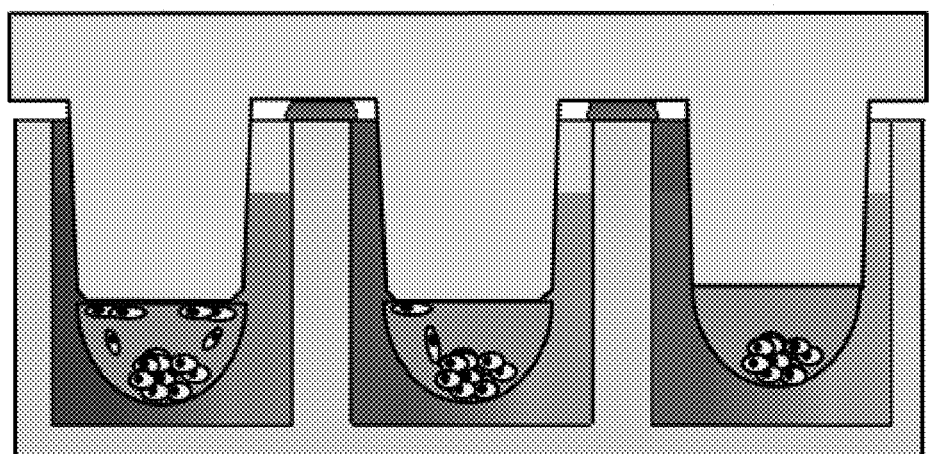
FIG. 4D shows an example of step S3 regarding cell invasion.

FIG. 4D shows an example of step (S3) regarding cell invasion.

Step (S3) according to the present invention includes steps of: (S3-1) withdrawing the micropillars 110, which have the formed cell spheroids thereon, from the microwells 210; (S3-2) inserting the micropillars 110 again into the microwells 210 containing a predetermined drug in a state in which the end contact surfaces 111 of the withdrawn micropillars 110 face downward; and (S3-3) allowing the cells contained in the cell spheroids to migrate, invade and adhere to the end contact surfaces 111 of the micropillars 110 inserted again.

The drug in step (S3-2) according to the present invention may be a cancer therapeutic agent.

Step (S4) according to the present invention is a step of staining and scanning the cell spheroids and the cells that invaded the end contact surfaces 111 of the micropillars.

FIG. 4E shows an example of step S4 regarding cell staining and scanning.

In the present invention, the cells may be labeled with a fluorescent protein such as green fluorescent protein (GFP). The labeling may be performed by transduction with the fluorescent protein gene inserted into a vector or the like, or by antibody staining.

Step S5 according to the present invention is a step of calculating the invasion ratio of cells by the following Equation 1 through the fluorescence image of the scanned cells.

$$\text{Invasion Ratio} = \frac{\text{Invasion cell area}}{\text{Total cell area}} = \frac{A_{Total} - A_{spheroid}}{A_{Total}} \quad \text{[Equation 1]}$$

wherein $A_{total}$ represents the total cell area corresponding to a low-intensity area (higher than 20 code green intensity), and $A_{spheroid}$ represents the spheroid area corresponding to a high-intensity area (exceeding 60 code green intensity).

EXAMPLES

The present invention will be described with a focus on an example of head and neck squamous cell carcinoma (HNSCC) below.

In vitro methods for measuring the extent of metastasis of head and neck squamous cell carcinoma (HNSCC) include wound healing, transwell, and organotypic assays. However, these are still lab-intensive and time-consuming tasks.

Accordingly, for the rapid detection and high throughput screening of invasiveness in 3D condition, the present invention proposes a novel spheroid invasion assay using a commercially available pillar platform system.

Head and neck squamous cell carcinoma (HNSCC) is the sixth most common cancer worldwide and the 5-year survival of patients with HNSCC is approximately 50%. Metastasis is a leading cause of the poor prognosis of HNSCC patients, and its underlying pathogenesis and mechanism are still the focus of intense investigation.

It is well recognized that the metastatic process has multiple steps: loss of cell-to-cell adhesion with increased cell motility (cell migration), invasion across the extracellular matrix (ECM), and the basement membrane of the blood vessels (intravasation), and extravasation into metastatic foci.

To develop or validate the diagnostic and therapeutic strategies (e.g., anti-cancer drug screening), several in vitro laboratory or in vivo animal models have been used to recapitulate multifactorial interactions between tumor and surrounding tumor microenvironment (TME).

Conventional in vitro experimental tools, such as wound healing assay or modified Boyden chamber assay, are easier to perform with a simple design, which allows a more controlled environment for repetitive and reproducible measurement of cancer cell migration and invasion, when compared with in vivo animal model.

However, the direct correlation of outcomes using in vitro assays with the biology of human cancer is disputed, mostly because of the limitations of a two-dimensional (2D) cell culture system, which lacks spatial and temporal components of a three-dimensional (3D) solid tumor.

When the fact that cancer cells grow and metastasize in the body with a 3D organization interacting with neighboring cancer cells as well as TME is taken into consideration, the invasion assay needs to reflect the 3D condition to precisely evaluate the invasive phenotype of cancer Accordingly, the present invention describes a novel, 3D pillar array system, in which Matrigel surrounded cancer spheroid on the tip of each pillar. For rapid quantification of the changes of invasive phenotype of cancer cells from the spheroids, simple staining and automated optical analysis is performed. To evaluate the clinical efficacy of this system, patient-derived cells (PDCs) of HNSCC patients were used after the validation experiments with immortalized cancer cell lines.

Material and Methods

Using the pillar-based spheroid invasion assay, migration and invasion was evaluated in three patient-derived cells (PDCs) of HNSCC. Immunofluorescence of live cells was used for the quantitative measurement of migratory and invaded cells attached to the pillar. A novel method for measuring cell metastasis was validated by measuring expression of epithelial-mesenchymal transition (EMT)-related gene (snail/2) by qRT-PCR. The present inventors also tested the impact of drug treatments (cisplatin, docetaxel) on cell migration.

Hereinafter, the materials and methods according to the present invention will be described in more detail.

Patient-Derived Cell Culture

Acquisition of PDC samples and the relevant experimental protocol was approved by the Institutional Review Board of Samsung Medical Center (SMC IRB file number 2015-06-132-008), and informed consent was obtained from patients. Also, this work was performed in compliance with all relevant ethical regulations and guidelines for research using human specimens. To introduce a spheroid into pillar/well chip platform, PDCs were acquired from HNSCC patients following informed consent. Detailed information on 3 HNSCC patients is presented in supplementary Table 1.

Tissues from primary tumors were dissected into small pieces and washed with PBS. The minced tissue was digested with Minimum Essential Medium (MEM, Welgene, Daegu, Korea) containing DNase I (0.2 mg/mL, Sigma-Aldrich), dispase (4 mg/mL, Sigma-Aldrich), and collagenase (3 mg/mL, Sigma-Aldrich) at 37° C. for 3 hours.

After the addition of 10 mL of MEM with 10% fetal bovine serum (FBS, Gibco, Grand Island, NY, USA) and 1× penicillin-streptomycin (P/S, Gibco), cell solutions were filtered using a cell strainer (70 μm Nylon, FALCON, 352350, NY, USA) to deplete unseparated tissue clusters. The cell solutions were centrifuged to collect HNSCC cells in the pellet. To increase the viability of primary cancer cells, ROCK inhibitor (Y-27632, Enzo life science, NY, USA) and fibroblast feeder cells were used to induce conditionally reprogrammed cells.

Specifically, single cancer cells were co-cultivated with mitomycin-C-treated Swiss 3 T3fibroblasts in F medium [3F-12 Nutrient Mixture (Ham): 1 Dulbecco's modified Eagle's medium (Welgene), 5% fetal bovine serum (Gibco), 0.4 μg/mL hydrocortisone (Sigma-Aldrich), 5 μg/mL insulin (Sigma-Aldrich), 8.4 ng/mL cholera toxin (Sigma-Aldrich), 10 ng/mL epidermal growth factor (Invitrogen), 24 μg/mL adenine (Sigma-Aldrich), and 10 μmol/L Y-27632 (Enzo Life Science, USA)]. Six-well plate containing $2 \times 10^5$ cancer cells per well were maintained in a 37° C. incubator.

Invasion (Metastasis) Assay

In the present invention, transwell for conventional invasion assay was used. The membrane of the transwell was coated with 100 μl Matrigel (Corning, NY, USA) basement membrane matrix diluted 9-fold. A549 cells ($2 \times 10^4$ cells/well) were seeded in the insert of the transwell with RPMI media without FBS. 500 μl RPMI media with FBS was filled in the wells to serve as a chemoattractant. After 24 h of cell incubation, migrated cells on the insert were fixed with 95% ethyl alcohol and then stained with 0.5% crystal violet.

Single Spheroid Formation in the Pillar Array

The commercially available pillar/well platform and its fabrication were reported previously. A pillar array was made by injection molding with polystyrene because of its high transparency, excellent biocompatibility, and adequate stiffness for injection molding in mass production. The plastic molding procedure was performed with an injection molder (Sodic Plustech Inc., USA). A single pillar array consisted of eight pillars, each measuring 2 mm in diameter, 9 mm in height, and 9 mm in the pillar-to-pillar distance, and thus the platform was compatible with conventional 96-well plates (FIG. 1A). Before using the pillar array, the pillar array and cell-encapsulation apparatus were immersed in 70% ethanol for 30 min for sterilization followed by complete drying at room temperature.

FIGS. 1 to 4 show an experimental protocol for spheroid invasion assay.

Figure 3:
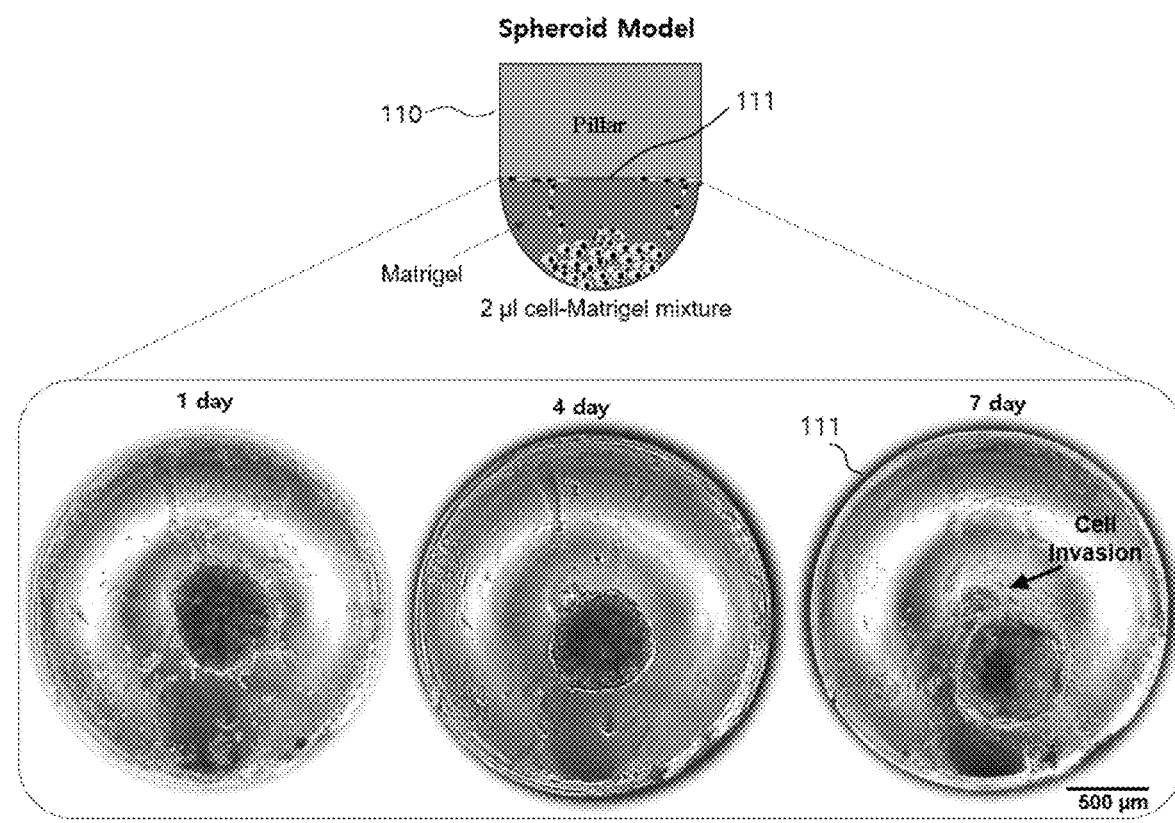
FIG. 3 shows a state in which cells migrate from a spheroid and adhere to the end contact surface of a micropillar.

FIG. 1 illustrates an example of a pillar array according to the present invention. FIG. 2 is a schematic view showing a state in which the pillar array according to the present invention is coupled to a well structure. FIG. 3 shows a state in which cells migrate from a spheroid and adhere to the end contact surface of a micropillar. FIGS. 4(a) to 4(c) show an example of step S2 regarding cell spheroid formation, FIG. 4(d) shows an example of step S3 regarding cell invasion, and FIG. 4(e) shows an example of step S4 regarding cell staining and scanning.

As illustrated in FIG. 4(a), a cell/Matrigel mixture was dispensed on the top of each pillar, and the pillars were put upside down so that cells in Matrigel could sink and gather on the curvature of Matrigel. The cells were incubated at 37° C. under 5% $CO_2$. Aggregated cells were immersed in the microwells containing growth media to make spheroids. The micropillars were inserted into the microwells, respectively. Drugs were dispensed into the wells and the spheroids were exposed to the drugs.

As shown in FIGS. 3 and 4(d), patient-derived cells (PDCs) were gathered in the curvature of Matrigel (day 1), formed spheroids (day 4), and migrated from the spheroid to the surface of the pillar (day 7).

At day 7, the cells migrated from the spheroid to the pillar and adhered to the surface of the pillar. The cells on the surface of the pillar were stained with Calcein AM, and fluorescence images of the spheroids and stained cells on the pillars were scanned for data analysis (see FIG. 4(e)).

In the image of FIG. 4(e), invasive cells migrated from the spheroid to the pillar and adhered to the surface of the pillar. Blue in the scanned image means the nucleus of adhered cells on the pillar.

To increase adhesion between the pillar surface and spheroid-containing Matrigel, the surface of each pillar was coated with poly-L-Lysine (PLL). As shown in FIG. 4(a), 2 μl of a mixture of PDCs and Matrigel (Corning, NY, USA) was dispensed on the pillar surface. A suspension of cells in Matrigel was prepared by mixing equal volumes of cell suspension in F-medium ($1\times10^7$ cells/mL) with Matrigel, to obtain a final concentration of $5\times10^6$ cells/mL and 50% alginate in the Matrigel. While changing the cell seeding density, the final Matrigel content remained constant at 50% throughout the experiment.

However, for FaDu cells, the final concentration of Matrigel should be reduced to 20% to ensure the definite invasive phenotype. Before gelling Matrigel, the pillar array was inserted into a blank 96-well plate and placed on ice to prevent Matrigel gelation. After 20 min, Matrigel containing the aggregated cells was cross-linked and gelled by transferring the pillar array in 37° C. incubation for 15 min. To form spheroids in Matrigel, the pillars were maintained upside down to obtain cells down for 4 days. After an average 7 days, spontaneous cell migration from the spheroid was observed, followed by invasion through the Matrigel and adhesion to the surface of the pillar (see FIG. 3).

For drug treatment, Docetaxel (Sigma-Aldrich, No. 01885), Cisplatin (Sigma-Aldrich, No. 1134357) and Staurosporine (Sigma-Aldrich, No. S4400) were purchased as powders and dissolved in dimethyl sulfoxide (Sigma-Aldrich, D2650). On the day of treatment, the drugs were thawed and diluted to the indicated concentrations using culture media. After confirming the formation of stable spheroids on the pillar, the culture medium was replaced with medium containing docetaxel, cisplatin, and staurosporine. Next, cultures were incubated for an additional three days to evaluate their impact on cell invasion.

To visualize spheroids as well as invasive cells inside Matrigel, the pillar array containing the spheroid was stained with 200 μl of 1 μM Calcein AM (Invitrogen, CA) and 1 μg/mL Hoechst 33,258 dissolved in PBS buffer for 60 min. Upon scanning, the green dots represented the cytosol of live cancer cells in Matrigel, and blue dots indicated nuclei of the attached cells on the surface of the pillar. The images were obtained at 4× magnifications with a 490-nm excitation filter and a 520-nm emission filter under a fluorescent microscope (OLYMPUS BX51). To verify cell invasion, the present inventors found a single layer of the cell nucleus in the stretched cell on the surface of the pillar as shown in the enlarged image of FIG. 4(e).

Cell Viability Assay

CellTiter-Glo® 3D (Promega, USA) assay was used for cell proliferation and drug response assays. The luminescence readings of drug-treated cells were corrected with the readings of the normal control. The cell survival percentage was normalized using the untreated cells as 100% cell survival.

Image Processing and Data Analysis

The green spots containing spheroid and invasive cells were imaged by an automatic optical fluorescence scanner (ASFA™ Scanner ST, Medical & Bio Device, South Korea). The intensity of green fluorescence was measured using an 8-bit code in three color channels with values of 0 to 255 representing 256 codes for each of the R (red), G (green), and B (blue) primary colors, and spheroid and invasive cells were identified depending on the intensity thresholds ranging from 20 to 60 code.

The spheroids were composed of many live cells with intensity exceeding 60 code due to cell accumulation, while invasive cells migrated and adhered to the surface of the pillar with a low intensity (less than 60 code) due to monolayer morphology of cells. The spheroid was easily distinguishable from Matrigel based on a higher-intensity area (>60 code) than Matrigel.

The total cells containing spheroids, as well as invasive cells, were measured by low-intensity area more than 20 code. To calculate the invasion ratio, invasive cells attached to the pillar surface were identified by subtracting the spheroid area (higher than 60 code green intensity) from total cell area, based on the following Equation 1.

$$\text{Invasion Ratio} = \frac{\text{Invasion cell area}}{\text{Total cell area}} = \frac{A_{Total} - A_{spheroid}}{A_{Total}} \quad \text{[Equation 1]}$$

wherein $A_{total}$ represents the total cell area corresponding to a low-intensity area higher than 20 code green intensity, and $A_{spheroid}$ represents the spheroid area corresponding to a high-intensity area exceeding 60 code green intensity.

A reagent mainly used for staining in the experiment is a reagent called Calcein-AM, which selectively stains only live cells with a green fluorescence dye. Because it emits green fluorescence, a fluorescence image is measured at a wavelength of 520 nm when measuring a signal with a fluorescence microscope. However, in the case of fluorescence, auto fluorescence is frequently included as a background.

In order to exclude this phenomenon and selectively recognize and analyze only live cells, the green fluorescence intensity code is adjusted as a threshold value in the analysis program. This determines which value is regarded as a live cell and which signal is regarded as a background, based on the intensity of the green signal.

In many cases, the green fluorescence intensity code was selected mainly based on the cell image observed under the optical microscope. Accordingly, in the present invention, only the cells attached to the end contact surfaces of the micropillars during cell incubation are processed in order to measure the migrated portion.

To this end, signals with low intensity are generally taken, and a signal of a cell spheroid is excluded. More specifically, since the cell spheroid is an aggregate of a plurality of cells, a relatively strong green signal can be measured. Accordingly, only a value of green fluorescence intensity code 60 or more may be taken and excluded from green fluorescence intensity code 20. That is, the green fluorescence intensity code 60 means to capture only cell spheroids, and the green fluorescence intensity code 20 means to capture both the cells attached to the end contact surface of the micropillars and the spheroids.

FIGS. 5 to 9 shows invasion assay of A549 cell line.

Figure 6:
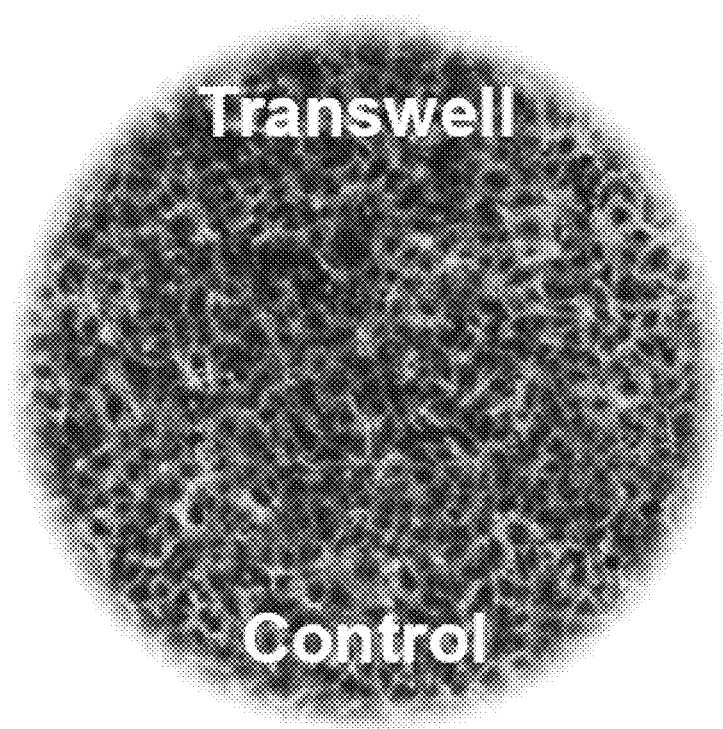
FIG. 6 shows invasion images of microwells.
Figure 6:
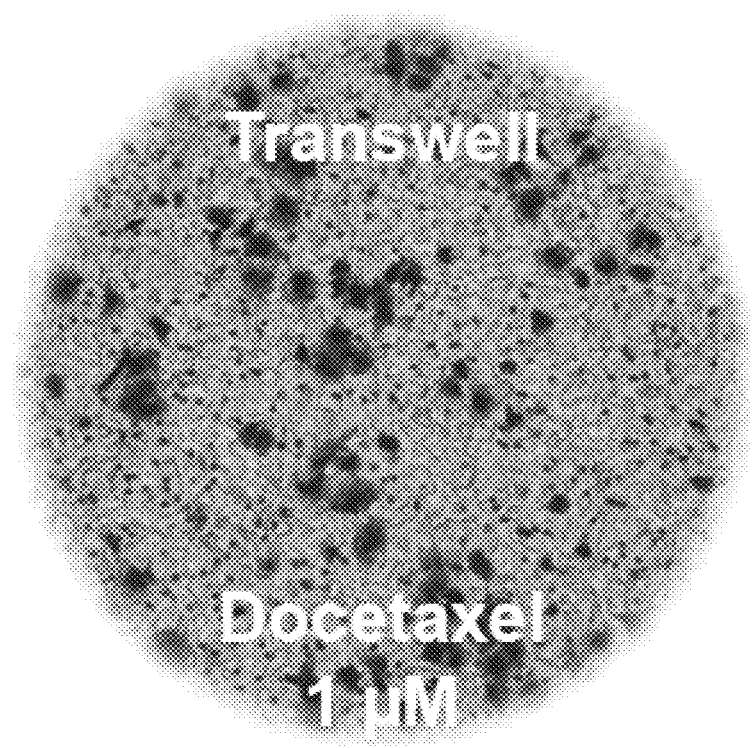
Figure 7:
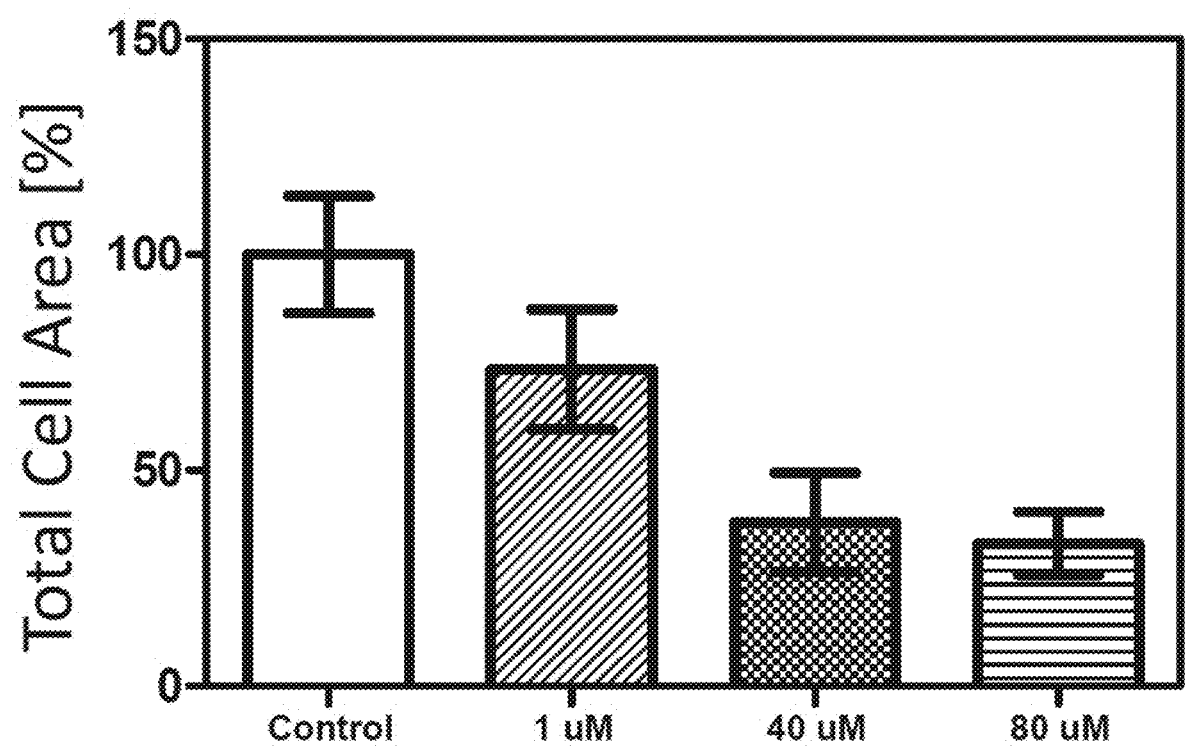
FIG. 7 shows the total cell area as a function of the docetaxel concentration.
Figure 8:
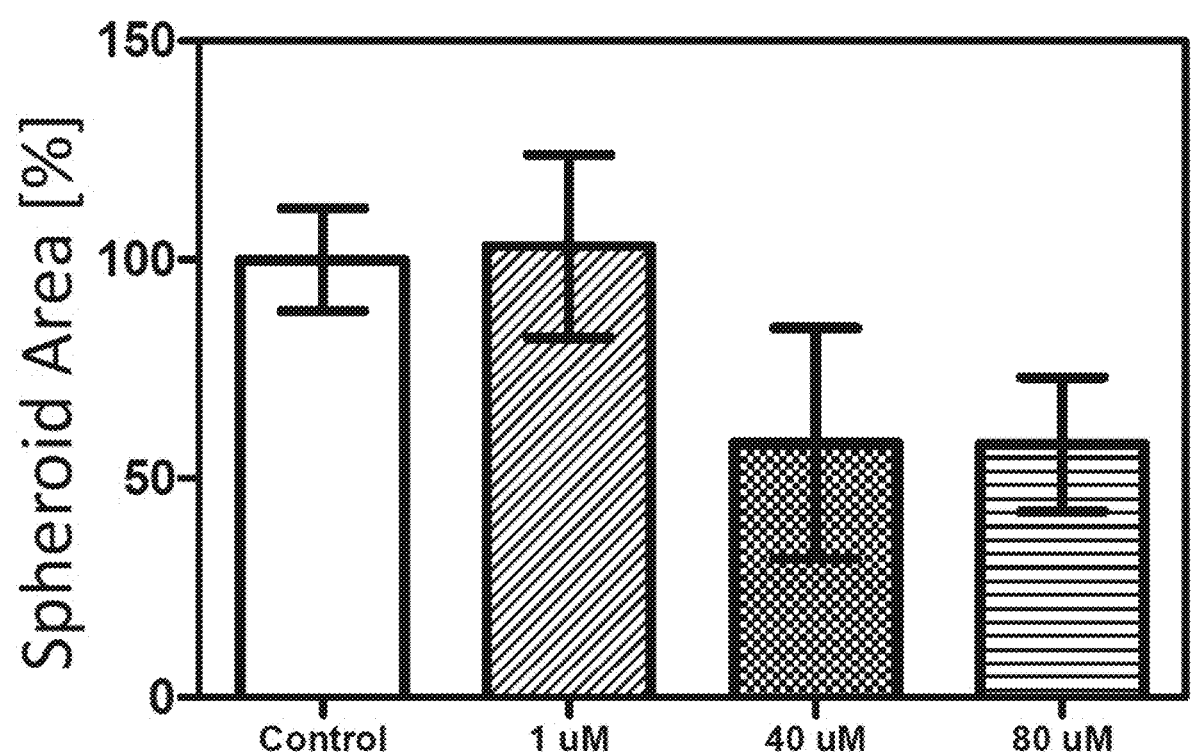
FIG. 8 shows the spheroid area as a function of the docetaxel concentration.
Figure 9:
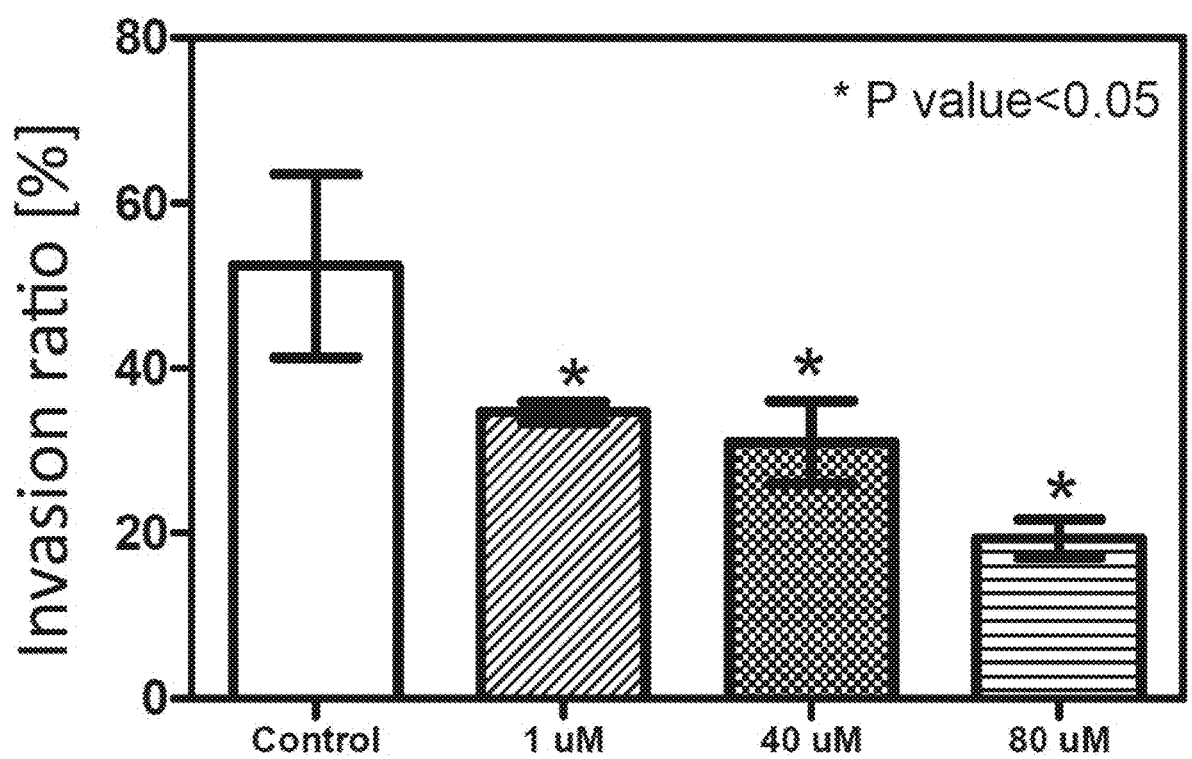
FIG. 9 shows the invasion ratio as a function of the docetaxel concentration.

Specifically, FIG. 5 shows images of viable spheroids on pillars with three different concentrations of docetaxel. FIG. 6 shows invasion images of microwells. FIG. 7 shows the total cell area as a function of the docetaxel concentration. FIG. 8 shows the spheroid area as a function of the docetaxel concentration. FIG. 9 shows the invasion ratio as a function of the docetaxel concentration.

Confocal Analyses

For whole-mount staining of spheroids on pillars in 96-well, spheroids were fixed with 4% PFA for 30 min on ice. After washing twice with PBS, samples were blocked with 5% donkey serum in 0.5% Triton X-100 in PBS (PBST) for 60 min at RT. Spheroids on pillars in 96-well were incubated overnight at 4° C. with primary antibodies (diluted at a ratio of 1:200 in blocking solution). After several washes with PBS, samples were incubated for 2 hours at RT with secondary antibodies and DAPI (diluted at a ratio of 1:500 in blocking solution). The following primary and secondary antibodies were used for immunostaining: anti-E cadherin (goat polyclonal, AF 748, R&D). FITC- or Cy3-conjugated secondary antibodies were purchased from Jackson ImmunoResearch. Nuclei were stained with DAPI (Invitrogen). Images were acquired using LSM700 or LSM770 confocal microscope (Carl Zeiss). Three dimensional analyses of the spheroids were performed with cross-sectional spheroid images using ZEN 2012 software (Carl Zeiss).

RNA Interference in FaDu Cell Line

After confirming the formation of stable spheroids on the pillar (4 days later), transfection of siRNAs was performed in 96-well culture with pillar using Lipofectamine RNAiMAX transfection reagent (Invitrogen). Invasion ratio was calculated after an average 7 days. The final concentration of siRNA was 10 nM. Non-specific scrambled siRNA was used for negative control. The siRNA sequences used in the present invention were as follows:

```
human Snai1#1
5'-AGACCCACUCAGAUGUCAAGAAGUA-3';

human Snai1#2,
5'-CCUGUCAGAUGAGGACAGUGGGAAA-3';
```

```
-continued
human Snai2#1,
5'-CCGUAUCUCUAUGAGAGUUACUCCA-3';

human Snai2#2,
5'-GAUGCAUAUUCGGACCCACACAUUA-3'.
```

Quantitative RT-PCR

The relative abundance of Snai1 and Snai2 mRNA was analyzed via quantitative real-time reverse transcription-polymerase chain reaction (qRT-PCR). Total RNA was extracted from homogenized original tumor tissues or FaDu cells using the RNeasy kit (Qiagen Valencia, CA), and the extracted RNA was reverse transcribed with Superscript III Reverse Transcriptase (Invitrogen, CA). Finally, real-time qRT-PCR was performed using a specific Taqman Gene Expression Assay (Applied Biosystems, MA, USA). Gene-specific primers and probes for the TaqMan gene expression assay were purchased from Applied Biosystems. This included three genes: SNAI1 (Hs00195591_m1) and SNAI2 (Hs00950344_m1). HPRT1 (Hs02800695_m1) was used for normalization. Each mRNA was expressed as arbitrary units defined as an n-fold difference relative to the control gene HPRT1 ($2\Delta Ct \times 100$, where $\Delta Ct$ represents the difference in threshold cycle between the control and target genes).

Statistical Analysis

Statistical significance was assessed by Student's t-test or by one-way analysis of variance (ANOVA) with Bonferroni post hoc test using SPSS 20.0 statistical software program. A two-sided p-value $>0.05$ was considered statistically significant.

Results

All PDCs successfully formed spheroid at 4 days and invasiveness thereof can be measured within 7 days. Intriguingly, one PDC (#1) showed robust migration, invasion and higher transcription of snail/2, compared to the other two PDCs. Furthermore, the invasion ratio of the control spheroids was about 70% while the invasion ratios of drug-treated spheroids were lower than 50%, and the difference showed statistical significance ($p<0.01$).

Invasion (Metastasis) Assay of A549 Cell Line in the Pillar Array

As can be seen in FIGS. 5 to 9, A549 cell line, which was usually used for 2D invasion assay, migrated from spheroid and adhered to the surface of the pillar. To verify invasion assay in the pillar array, A549 having high mobility for invasion assay was used in the first experiment. In no drug treatment, cells surrounding spheroids adhered to the pillar. Thus, those cells surrounding spheroid were faintly stained (see FIG. 2).

Based on the fluorescence intensity, spheroid was identified, and invasive cells were calculated by subtracting the spheroid area from the total cell area. A549 cells formed a spheroid two days after cell aggregation and incubation. Cells surrounding spheroid migrated for an additional three days of culture. To check the invasiveness of A549 cells, the present inventors conducted invasion assay using Transwell (24-well transwell, Cat. No. 3422, Corning, USA) in no drug and 1 µM Docetaxel.

FIG. 6 shows a state in which A549 migrated through the Matrigel-coated membrane, which means high invasiveness. However, 1 µM docetaxel inhibited the invasion of A549 in the Transwell as shown in FIG. 6. With total cell area (FIG. 7) and spheroid area (FIG. 8), the invasion ratio was calculated, and in control, it was 52%, while one in docetaxel was lower than 35% (FIG. 9). In the Transwell, cell viability did not measure. However, the pillar-based spheroid invasion model gave cell viability due to living cell staining. Total cell area, which means cell viability, also decreased depending on docetaxel concentration. The experiment in the present invention also shows docetaxel reduced the size of a single big spheroid as well as inhibited cell invasion.

Invasive Phenotypes of FaDu Cell Line in the Pillar Array

Next, FaDu cells line, which is a HNSCC cell line, was used to evaluate invasiveness in 3D pillar array system. Spheroid formation was confirmed 4 days after incubation (FIG. 3A) and invasive FaDu cells from spheroid were detected for an additional three days of culture (FIG. 10B) in 20% Matrigel, which is different into A549 experiment. Using confocal microscopy, it was confirmed that the expression of E-cadherin, which is a typical epithelial-mesenchymal transition (EMT) marker and is usually decreased during EMT process, decreased in invading cells from spheroid (FIG. 3C), reflecting invasive and metastatic phenotypes of HNSCC.

Additionally, cross-sectional analysis by 3D reconstruction demonstrated that the present method calculating the invasiveness using Equation 1 is quite reasonable, because the direction of invasive cells from the spheroid is mostly facing the lateral side than the topside of the pillar surface. As Snai1 and Snai2 are well known EMT regulators in many cancer cells, the present inventors sought to examine the impact of Snai1/Snai2 on invasiveness of FaDu cells upon transfection with the siRNAs. As expected, 3D spheroid pillar assay using FaDu cells transfected with Snai1/Snai2 siRNA showed suppressed invasiveness from spheroid (see FIGS. 11 and 12), with significant decrease in endogenous Snai1/Snai2 level in FaDu cell line (see FIG. 13), suggesting possibility that the system of the present invention can serve as a reliable anti-cancer effect screening tool.

As described above, FIGS. 10 to 13 show the invasiveness of FaDu cell line.

Figure 10A:
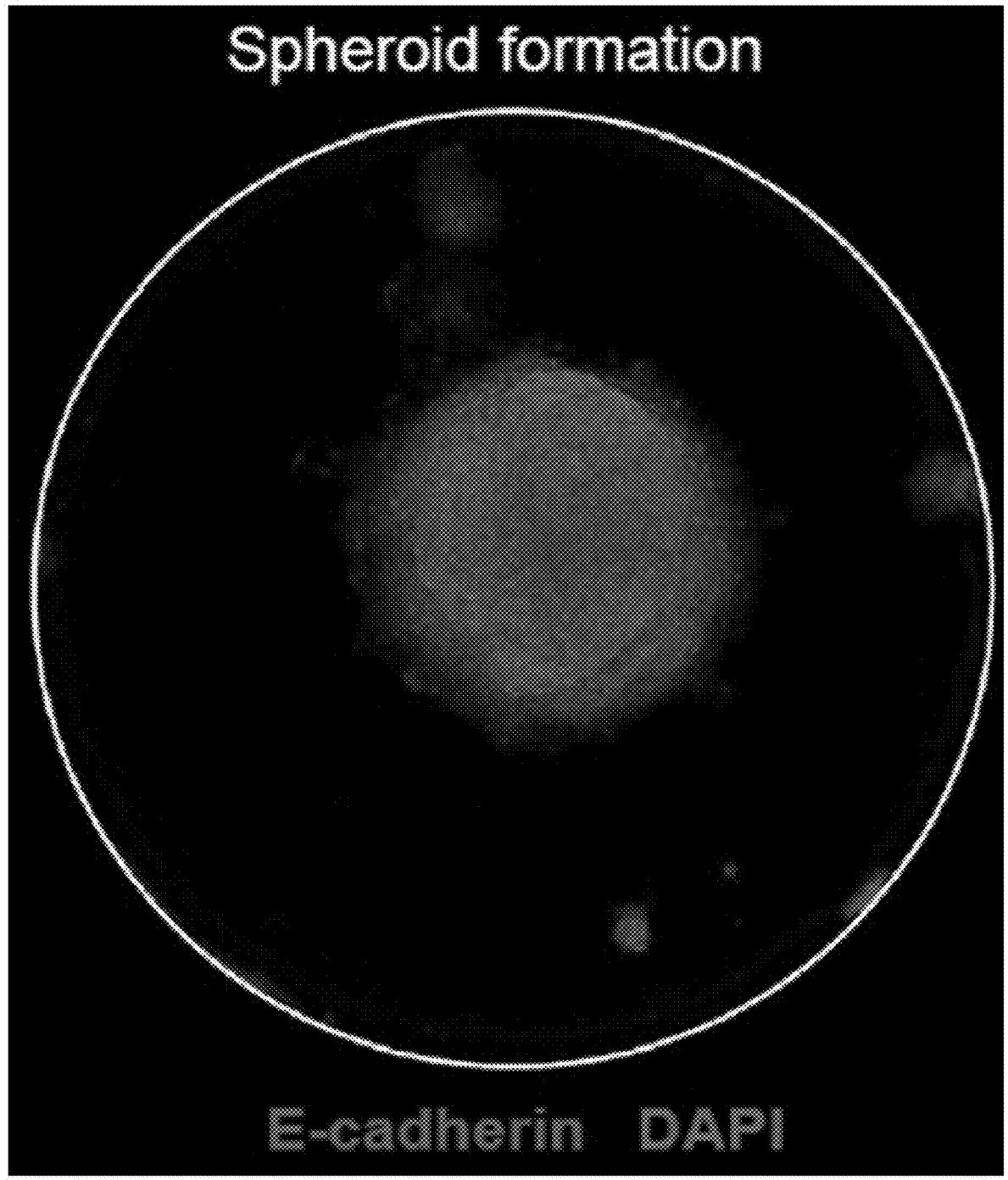
Figure 12:
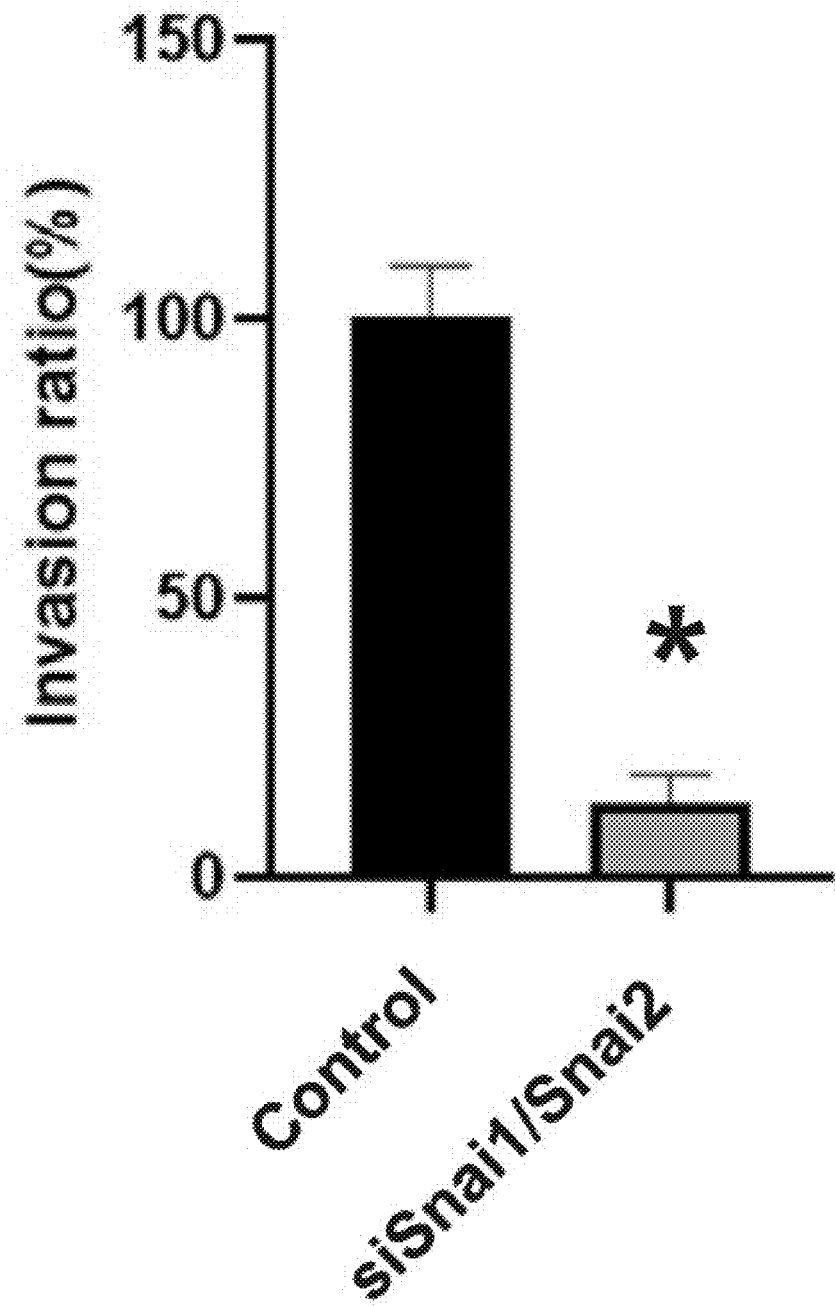
FIGS. 12 and 13 respectively show the invasion ratio according to siRNA-treated cells and the mRNA levels of Snai1 and Snai2 examined by qRT-PCR following knockdown.
Figure 13:
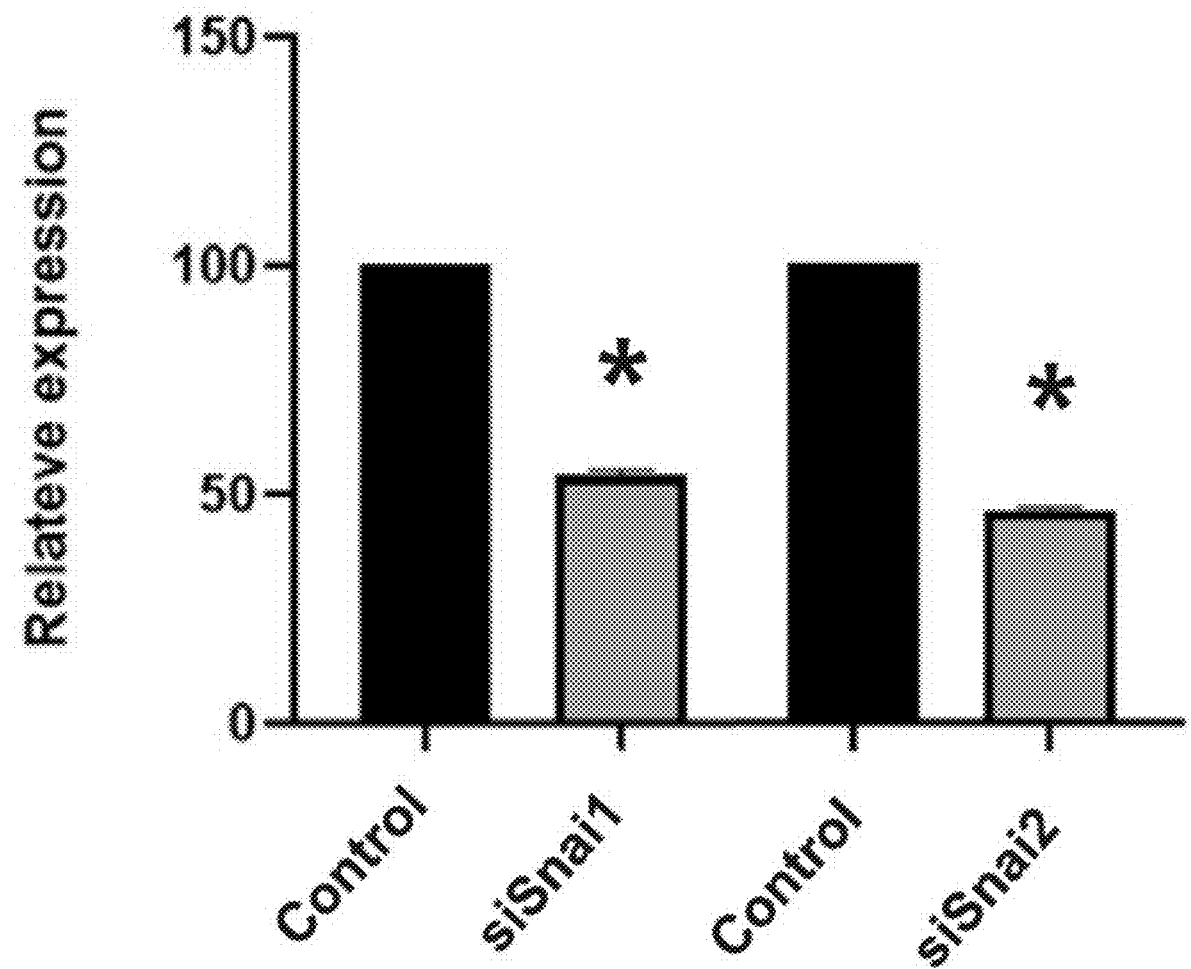

FIG. 10A shows representative images of E-cadherin expressions (red) in FaDu spheroid using pillar assay, and FIG. 10B depicts image showing invaded FaDu cells from spheroid. Here, arrows indicate invaded FaDu cells with decreased E-cadherin expression. FIG. 11 shows invasion assays performed on FaDu cells transfected with Snai1 and Snai2 siRNAs. FIGS. 12 and 13 respectively show the invasion ratio according to siRNA-treated cells and the mRNA levels of Snai1 and Snai2 examined by qRT-PCR following knockdown.

Invasive Phenotypes of HNSCC Spheroids in the Pillar Array

Figure 14:
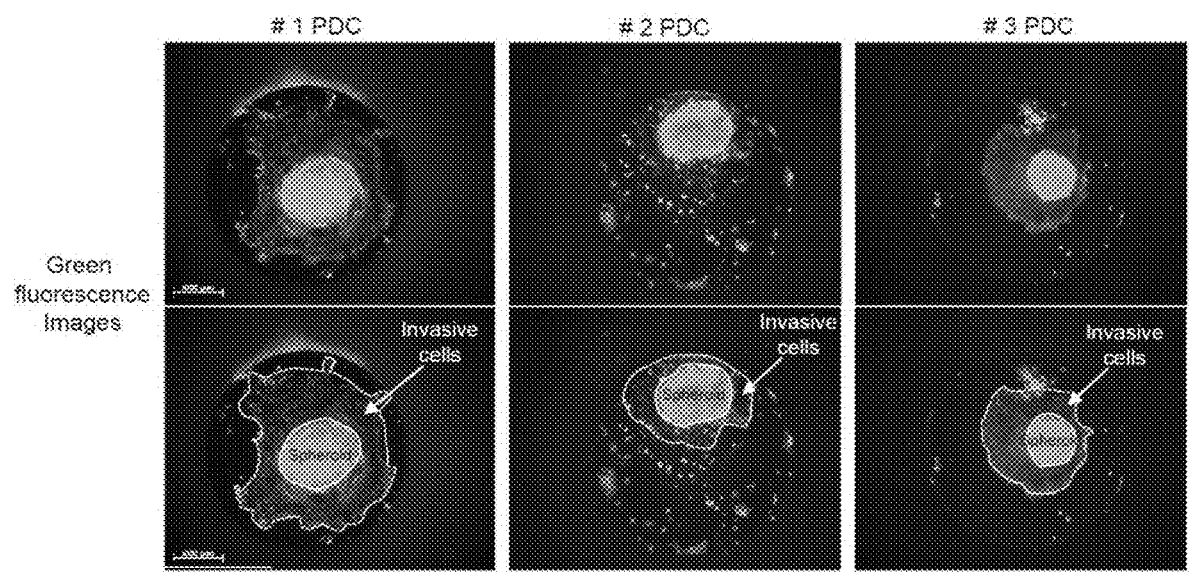
FIG. 14 shows images of the spheroid in each PDC.
Figure 15:
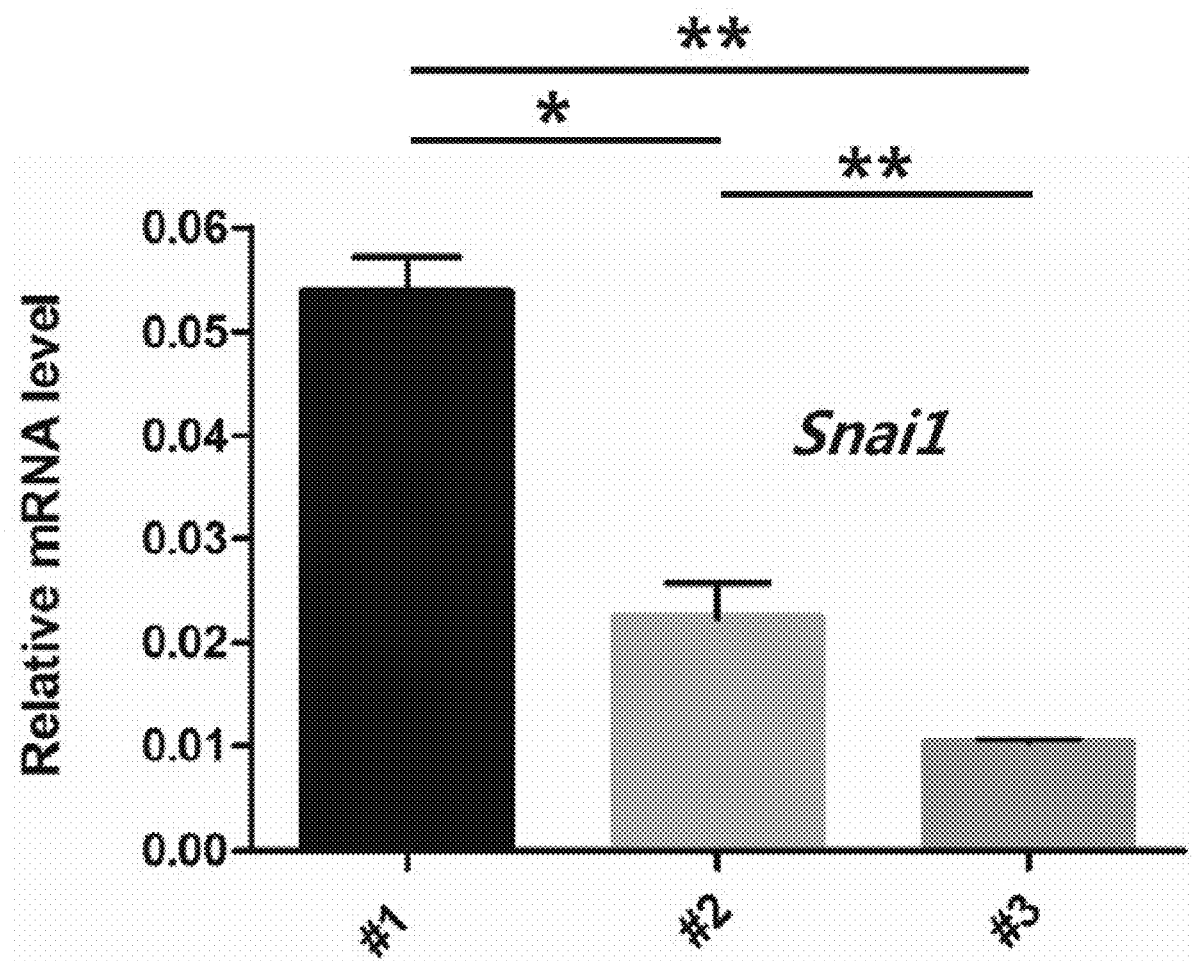
FIGS. 15 and 16 show comparisons of mRNA expressions of EMT-related genes (Snai1 and Snai2) by qRT-PCR analysis in primary tumor cells from 3 patients with head and neck squamous cell carcinomas, wherein the data thereof were normalized to Hprt1.
Figure 16:
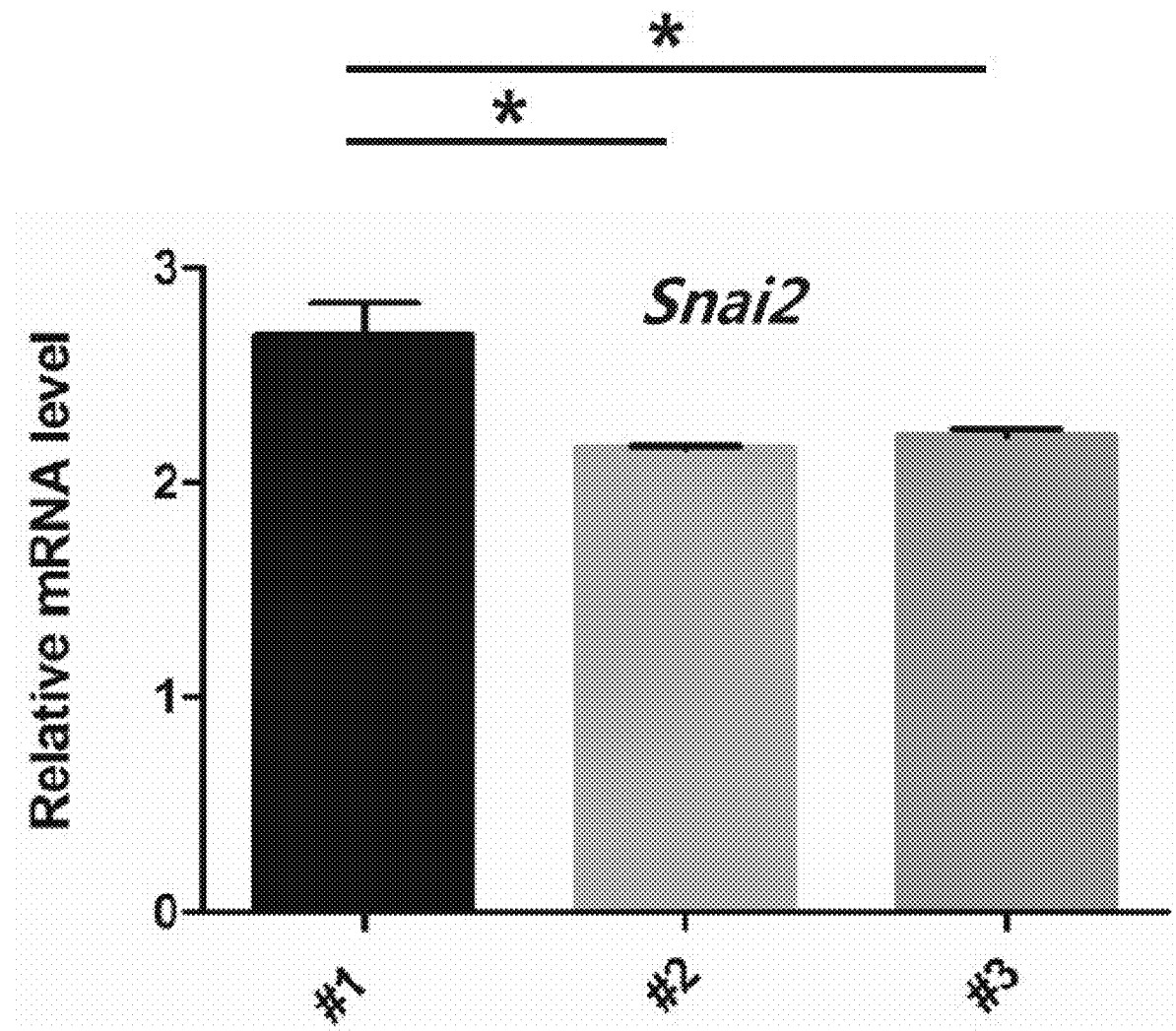

FIG. 14 shows images of the spheroid in each PDC. FIGS. 15 and 16 show comparisons of mRNA expressions of EMT-related genes (Snai1 and Snai2) by qRT-PCR analysis in primary tumor cells from 3 patients with head and neck squamous cell carcinomas. Here, data were normalized to Hprt1.

As illustrated in FIGS. 14 to 16, the three HNSCC spheroids showed different invasive phenotypes in the pillar array. All HNSCC PDCs formed spheroids successfully in Matrigel after four days of cell aggregation and incubation. During additional three days of culture, only one PDC (#1 PDC) migrated from spheroid and adhered to the pillar surface, as shown in bright and green fluorescence microscopic images (FIG. 14A). The adhered cells formed a monolayer on the pillar surface, and the intensity of cells was lower than the intensity of spheroid itself comprising many cells. The other two PDCs showed spheroid outgrowth and expansion only without noticeable cell migration. Interestingly, #1 PDC, which showed robust migration and invasion from spheroid, was obtained from a patient with the most advanced cancer stage and cervical lymph nodal metastasis compared to the other 2 PDCs. Accordingly, the #1 PDC showed higher mRNA expression levels of EMT-related genes (Snai1, Snai2) compared to the other 2 PDCs, which were well recognized and related to invasive and metastatic phenotypes of HNSCC.

Varying Responses of HNSCC Spheroids to Therapeutic Drugs

Figure 17:
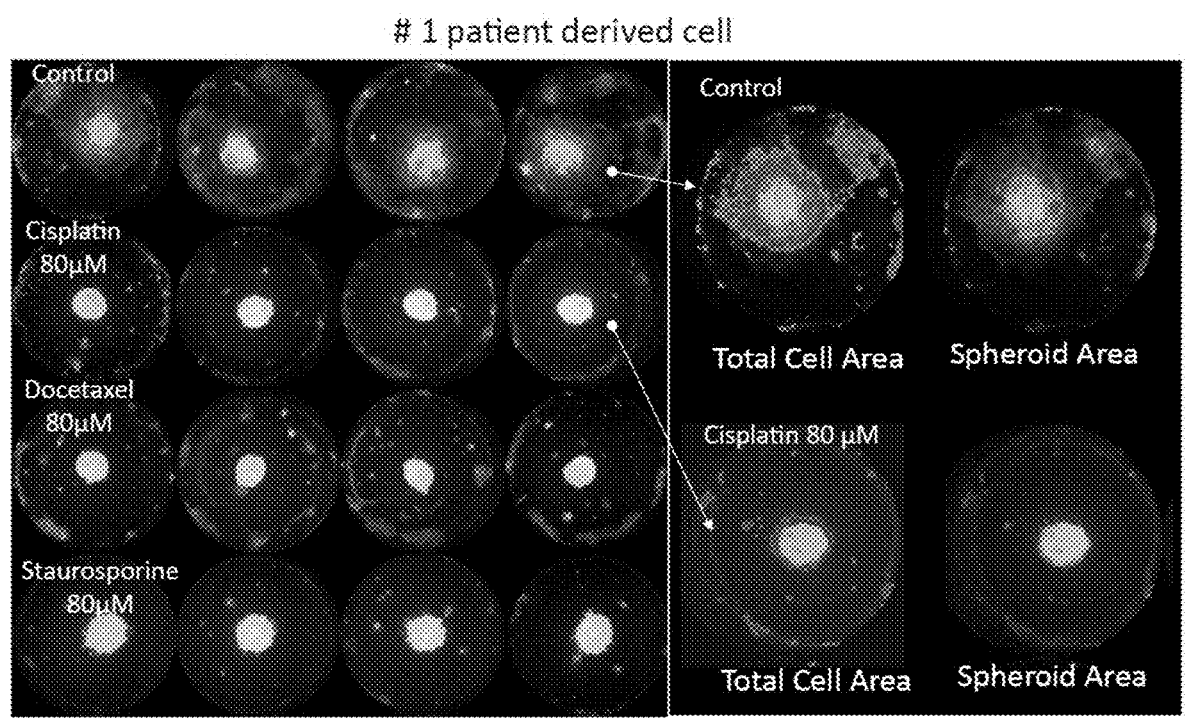
FIG. 17 shows the viable spheroid images on the pillar with three drugs, in which, from the image, invasive cells migrated from spheroid were extracted by dividing the invasion cell area with the total cell area depending on drugs.
Figure 18:
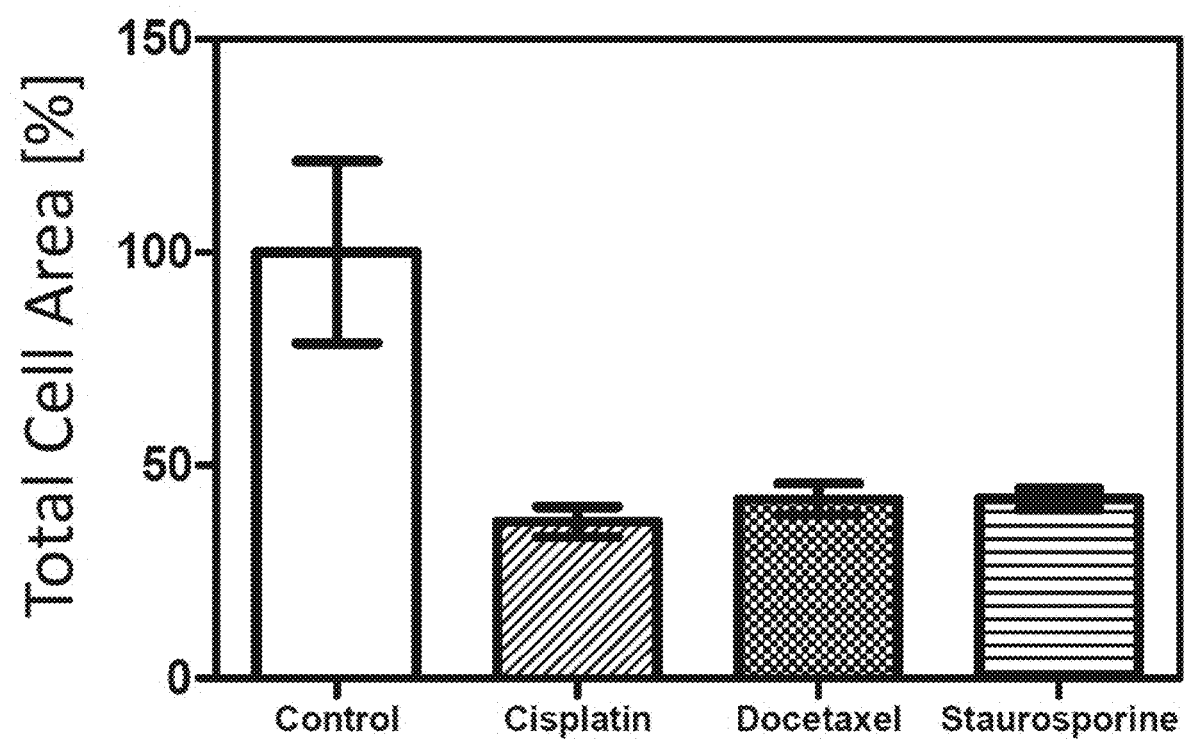
FIG. 18 shows the total cell area depending on to drugs.
Figure 19:
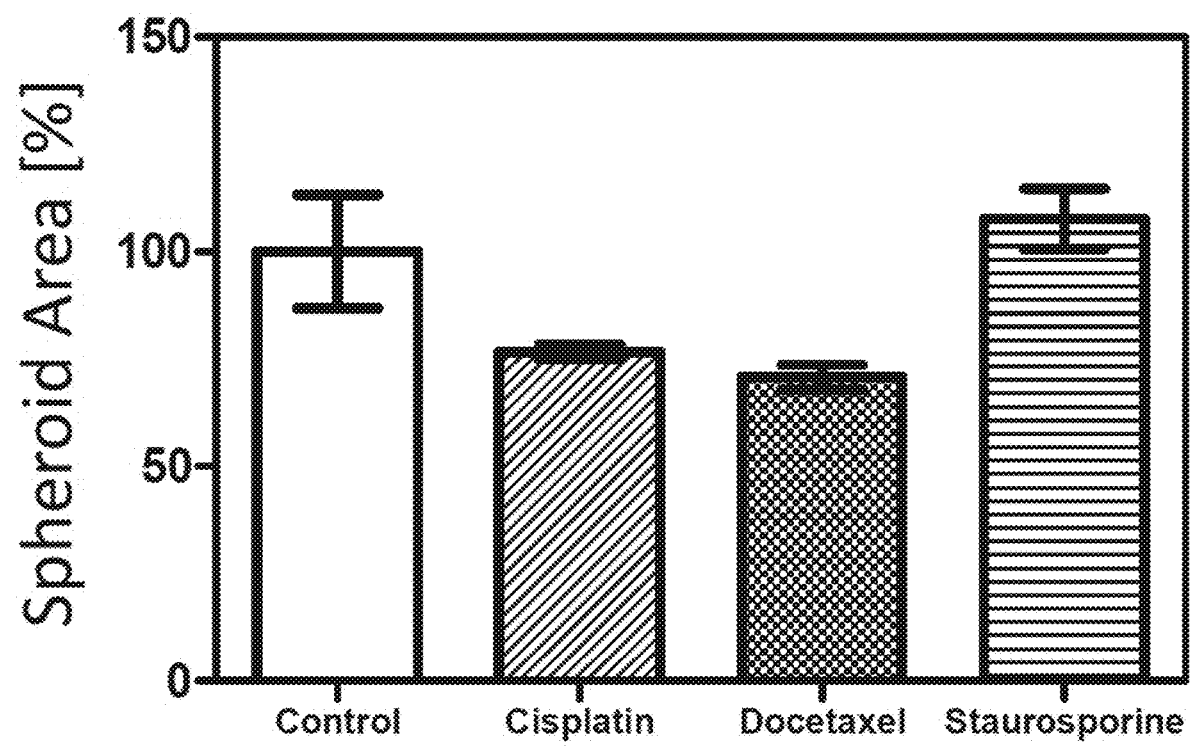
FIG. 19 shows the spheroid area depending on drugs.
Figure 20:
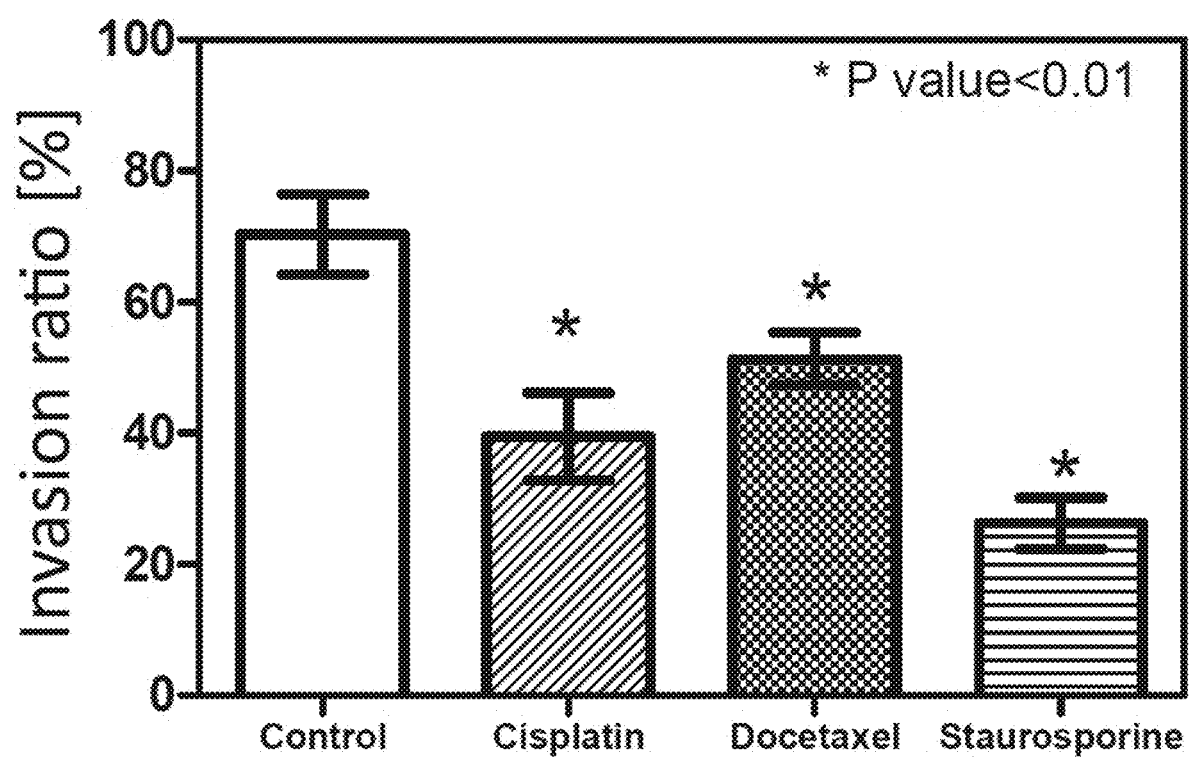
FIG. 20 shows the invasion ratio depending on drugs.

FIGS. 17 to 20 show invasion assay of #1 PDC (patient-derived Cell). Specifically, FIG. 17 shows the viable spheroid images on the pillar with three drugs. From the image, invasive cells migrated from spheroid were extracted by dividing the invasion cell area with the total cell area depending on drugs. FIG. 18 shows the total cell area depending on to drugs. FIG. 19 shows the spheroid area depending on drugs. FIG. 20 shows the invasion ratio depending on drugs.

To evaluate the impact of cancer-therapeutic drugs on the invasive phenotype of HNSCC PDCs, spheroids were treated with cisplatin and docetaxel, the two most commonly used antineoplastic agents in HNSCC, and with staurosporine, the cytotoxic agent acting as a positive control.

In view of the higher drug resistance in 3D spheroid cultured cells and the drug sensitivity assay results of cisplatin in PDC spheroid cultures, the present inventors treated the cells with 80 µM of drugs to observe inhibition of the invasion.

In the case of #1 HNSCC PDC, the spheroid morphology in control (no drug treatment) was faint and cloudy, which indicated spontaneous cell migration through Matrigel (FIG. 20). However, spheroids, treated with cisplatin, docetaxel, or staurosporine, clearly maintained circular shapes and borders, indicating that each drug effectively inhibited cell migration/invasion. The present invention showed that docetaxel suppressed the invasiveness of cells in head and neck cancer patients.

When three parameters (total cell area, spheroid area, and invasion ratio) were extracted and calculated from images, the invasion ratio of the control spheroids was about 70% while the invasion ratios of drug-treated spheroids were lower than 50%, and the difference showed statistical significance (p-value <0.01) (FIGS. 18 to 20).

In contrast to #1 HNSCC PDC, invasive phenotypes of #2 and #3 HNSCC PDCs were not distinct in control as well as drug-treated spheroids, and thus the invasion ratios remained at around 20 to 50%, regardless of drug treatments, suggesting that the response of cancer cells to the drug could be diverse depending on their migration and invasive potency.

Discussion

The presented spheroid invasion assay using pillar array could be useful for the evaluation of cancer cell behavior and physiology in response to diverse therapeutic drugs.

To date, various techniques for evaluating cancer cell invasiveness have been addressed and validated for the progression and prognosis of HNSCC. Notably, recent advances in bioengineering technology enable diverse platforms, mimicking the interaction between tumor and TME. For example, cancer organoids or spheroids are formed via a hanging-drop method or within a U-shaped well plate. Then, the spheroids are imbedded into ECM, such as collagen or Matrigel, to study changes in cancer-specific phenotypes in response to TME modulation (see FIG. 21). Microfluidic chip is also one of the promising tools for exploring TME parameters and their role in cancer invasiveness, due to its feasibility to control 3D environments.

Despite several advantages of biotechnology-driven platforms including microfluidic models, however, it is still not easy to utilize them in actual investigations of cancer biology for the following reasons:

(1) Most microfluidic models require specialized experience and facilities in bioengineering to perform and interpret the experiment; (2) quantitative measurement of migrated and invaded cells in 3D design should be reproducible; however, it may be challenging because tracking the stretched cells with confocal scanning or counting embedded spheroids in ECM is a lab-intensive and time-consuming task; and (3) technical validation of 3D platform with patient-derived cells (PDCs) is necessary to prove its physiological relevance with clinical oncology.

Figure 21:
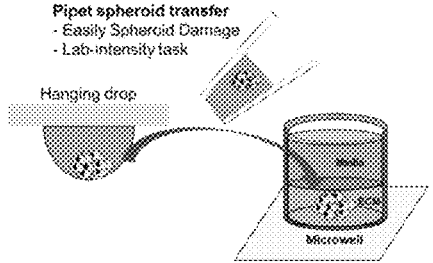
FIG. 21 shows a comparison between a conventional art and the present invention.

FIG. 21 shows a comparison between a conventional art and the present invention. Specifically, FIG. 21(a) shows conventional well-based spheroid invasion model, and FIG. 21(b) pillar array containing 2-mm diameter pillars according to the present invention.

The present invention describes a spheroid invasion (invasion) assay using a pillar array, in which Matrigel surrounds spheroid on the tip of each pillar (see FIG. 21(b)). In the conventional method, spheroid moves to Matrigel and the stretched cells from the spheroid is tracked, and this method is a lab-intensive and time-consuming task (see FIG. 21(b)).

The pillar-based spheroid invasion model according to the present invention easily induced spheroid formation on the pillar. Besides, the spheroid was induced by naturally-aggregated cells on the pillar within Matrigel, and the average size of each spheroid was higher than 500 μm, which means that the spheroid formation process mimics the physiology of solid tumor in humans (FIG. 21(b)).

After seven days of spheroid formation and growth, spontaneous migration of cancer cells from spheroid and their invasion through Matrigel was observed, and then the migrated cancer cells finally adhered to the surface of the pillar. To evaluate the invasiveness, the present inventors just stained live-cell attached to the pillars in the pillar-based spheroid invasion model to evaluate invasiveness. Therefore, this pillar system array not only recapitulates the biological environment of solid tumor in an in vitro model, but also overcome the low throughput of previous 3D cell-based invasion assays.

Clinically, it is well known that each cancer cells have a different invasive phenotype even in the same kind of squamous cell carcinoma, and the cancer cells harboring EMT behavior play a critical role in the determination of the clinical outcome of cancer patients. In the present invention, the present inventors also observed spontaneous migration and invasion of three head and neck patient's cancer cells, corresponding to each patient's cancer stage and mRNA expression of EMT-related genes. Thus, the current platform is clinically applicable for evaluating cancer invasiveness because it was confirmed that the system of the present invention worked well with PDCs for the invasion assay.

Current chemotherapy for HNSCC patients is based on cisplatin and docetaxel, in combination with radiation. However, despite conventional therapy, a subset of the patients exhibits an increased risk of recurrence and death. Primarily, cancer cells developing drug resistance are associated with poor prognosis. In this context, the present inventors confirmed that the pillar array was beneficial to test the impact of drug treatments on the changes in cancer invasiveness as well as cell viability. Thus, quantification for invasiveness using a 3D pillar array system could be taken into consideration in treatment decisions and drug choice.

In the present invention, the present inventors have successfully established a whole mount immunofluorescence staining by confocal microscopy in the 3D pillar array system of the present invention, which is essential to analyze the patterns and behavior of the cells. Furthermore, using applicable antibodies, it could be possible to conduct spatiotemporal analyses or mechanical studies in various cell types. Another useful aspect of this method is that once the concentration of Matrigel is established, it is possible to evaluate the invasiveness easily from various cell types. Thus, the 3D pillar array system of the present invention could be applicable and generalized in many other laboratorial setting. Future studies of the present inventors will include the set-up of a co-culture model of cancer spheroids with the components of TME, such as cancer-associated fibroblasts or tumor-infiltrating lymphocytes, and test the impact of various therapeutic drugs. Also, the evaluation of ionizing radiosensitivity of patient-derived spheroids in an in vitro model is a practical tool to improve oncologic outcomes of cancer patients. In addition, the present inventors are still investigating the optimal culture conditions to increase the drug sensitivity of this pillar system such as using less PDCs for a smaller spheroid formation or direct spheroid formation system by eliminating the cell expansion process, which will make the pillar system of the present invention a more feasible and practical tool for drug testing.

In conclusion, the presented spheroid invasion assay using pillar array allowed easy quantification for the evaluation of cancer cell behavior and physiology in response to diverse therapeutic drugs.

The embodiments described herein and the accompanying drawings merely illustrate some of the technical ideas included in the present invention. Accordingly, the embodiments disclosed herein are not intended to limit the technical spirit of the present invention but to explain it, and thus it is obvious that the scope of the technical spirit of the present invention is not limited by these embodiments. Therefore, all modifications and specific embodiments that can be easily inferred by those skilled in the art within the scope of the technical spirit included in the specification and drawings of the present invention should be construed as falling within the scope of the present invention.

DESCRIPTION OF REFERENCE CHARACTERS

100: pillar array
110: micropillars
111: end contact surfaces
200: well structure
210: microwells

What is claimed is:

1. A method of measuring cell migration by measuring an invasion ratio of cells incubated on a pillar array inserted into a well structure, the method comprising steps of:
   - (S1) preparing a pillar array having a plurality of micropillars and a well structure having a plurality of microwells into which the plurality of micropillars is insertable, respectively;
   - (S2) forming cell spheroids by incubating cells in an extracellular matrix attached to end contact surfaces of the micropillars of the pillar array;
   - (S3) allowing the cells contained in the cell spheroids to invade the end contact surfaces of the micropillars;
   - (S4) staining and scanning the cell spheroids, the cells contained in the cell spheroids, and the cells that invaded the end contact surfaces of the micropillars; and
   - (S5) calculating the invasion ratio of cells by the following Equation through a fluorescence image of the scanned cells:

$$\text{Invasion Ratio} = \frac{\text{Invasion cell area}}{\text{Total cell area}} = \frac{A_{Total} - A_{spheroid}}{A_{Total}} \quad [\text{Equation}]$$

wherein $A_{total}$ represents a total cell area, and $A_{spheroid}$ represents a spheroid area, and wherein step (S2) comprises steps of:
   - (S2-1) placing the pillar array so that the end contact surfaces of the micropillars face upward, and dispensing and attaching the cell-containing extracellular matrix to the end contact surface surfaces;
   - (S2-2) placing the pillar array upside down so that the end contact surfaces of the micropillars face downward, and gathering the cells by maintaining the end contact surfaces in the downward-facing state for a predetermined time in a state in which the micropillars are inserted or not inserted into the microwells; and
   - (S2-3) inserting the micropillars into the microwells containing a culture medium in a state in which the end contact surfaces face downward, and forming cell spheroids by incubating the cells contained in the extracellular matrix.

2. The method of claim 1, wherein the extracellular matrix comprises Matrigel.

3. The method of claim 1, wherein, in step (S2-2), the state in which the end contact surfaces of the micropillars face downward is maintained at 4° C. for 20 minutes.

4. The method of claim 1, wherein, in steps (S2-2) and (S2-3), the cells are gathered at a lower end of the extracellular matrix.

5. The method of claim 2, wherein, in step (S2-3), the incubating is performed at 37° C. under 5% $CO_2$.

6. The method of claim 1, wherein, in step (S3), $A_{total}$ represents the total cell area corresponding to a low-intensity area higher than 20 code green intensity, and $A_{spheroid}$ represents the spheroid area corresponding to a high-intensity area exceeding 60 code green intensity.

7. The method of claim 1, wherein step (S3) comprises steps of:
   - (S3-1) withdrawing the micropillars, which have the formed cell spheroids thereon, from the microwells;
   - (S3-2) inserting the micropillars again into the microwells containing a predetermined drug in a state in which the end contact surfaces of the withdrawn micropillars face downward; and
   - (S3-3) allowing the cells contained in the cell spheroids to migrate, invade and adhere to the end contact surfaces of the micropillars inserted again.

8. The method of claim 7, wherein the drug in step (S3-2) is a cancer therapeutic agent.

* * * * *